United States Patent
Schneider et al.

(10) Patent No.: US 10,737,062 B2
(45) Date of Patent: Aug. 11, 2020

(54) AUTO LOCK FOR CATHETER HANDLE

(71) Applicant: St. Jude Medical, Atrial Fibrillation Division, Inc., St. Paul, MN (US)

(72) Inventors: Clint Schneider, Plymouth, MN (US); Joshua L. Dudney, Minneapolis, MN (US); Richard E. Stehr, Stillwater, MN (US); Troy T. Tegg, Elk River, MN (US); Michael C. Bednarek, Buffalo, MN (US); Guy P. Vanney, Blaine, MN (US); James A. Jensen, Plymouth, MN (US); Michael W. Stine, Long Prairie, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 326 days.

(21) Appl. No.: 15/615,255

(22) Filed: Jun. 6, 2017

(65) Prior Publication Data
US 2017/0312482 A1 Nov. 2, 2017

Related U.S. Application Data

(63) Continuation of application No. 14/311,525, filed on Jun. 23, 2014, now Pat. No. 9,694,159, which is a
(Continued)

(51) Int. Cl.
*A61M 25/01* (2006.01)
(52) U.S. Cl.
CPC .... *A61M 25/0136* (2013.01); *A61M 25/0147* (2013.01); *A61M 2025/0186* (2013.01)
(58) Field of Classification Search
CPC .......... A61M 25/0136; A61M 25/0147; A61M 25/0105
See application file for complete search history.

(56) References Cited

U.S. PATENT DOCUMENTS

| 4,196,730 A | 4/1980 | Wilson |
| 4,203,430 A | 5/1980 | Takahashi |
| (Continued) | | |

FOREIGN PATENT DOCUMENTS

| EP | 1205208 | 5/2002 |
| GB | 1170018 | 11/1969 |
| (Continued) | | |

OTHER PUBLICATIONS

Standard Handbook of Machine Design, ref. p. 6.40 Section 6.7 (Table 6.15), 10 pgs, Digital Engineering Library, www.digitalengineeringlibrary.com, 2004.
(Continued)

*Primary Examiner* — Emily L Schmidt
(74) *Attorney, Agent, or Firm* — Wiley Rein LLP

(57) ABSTRACT

The present invention is a catheter actuation handle for deflecting a distal end of a tubular catheter body, the handle including an auto-locking mechanism. The handle comprises upper and lower grip portions, an actuator, and an auto-locking mechanism. The auto-locking mechanism is adapted to hold a deflected distal end of the catheter in place without input from the operator. When the distal end of the catheter is deflected from its zero position, it typically will seek a return to its zero position, and as a result exerts a force on the actuator. The auto-locking mechanism acts by providing a second force that resists this force from the distal end and holds the distal end in place. As a result, the operator does not need to maintain contact with the buttons to maintain the distal end 18 in a set position once placed there by actuating the actuator.

16 Claims, 19 Drawing Sheets

Related U.S. Application Data continuation of application No. 11/646,744, filed on Dec. 27, 2006, now Pat. No. 8,777,929, which is a continuation-in-part of application No. 11/170,550, filed on Jun. 28, 2005, now Pat. No. 7,465,288.

(60) Provisional application No. 60/801,464, filed on May 17, 2006.

(56) References Cited

U.S. PATENT DOCUMENTS

| | | |
|---|---|---|
| 4,960,134 A | 10/1990 | Webster, Jr. |
| 5,125,895 A | 6/1992 | Buchbinder et al. |
| 5,125,896 A | 6/1992 | Hojeibane |
| 5,269,115 A | 12/1993 | Stentenbach |
| 5,269,757 A | 12/1993 | Fagan et al. |
| RE34,502 E | 1/1994 | Webster, Jr. |
| 5,277,199 A | 1/1994 | DuBois et al. |
| 5,281,217 A | 1/1994 | Edwards et al. |
| 5,318,525 A | 6/1994 | West et al. |
| 5,327,889 A | 7/1994 | Imran |
| 5,327,905 A | 7/1994 | Avitall |
| 5,327,906 A | 7/1994 | Fideler et al. |
| 5,330,466 A | 7/1994 | Imran |
| 5,342,295 A | 8/1994 | Imran |
| 5,354,297 A | 10/1994 | Avitall |
| 5,364,351 A | 11/1994 | Heinzelman et al. |
| 5,383,923 A | 1/1995 | Webster, Jr. |
| 5,389,073 A | 2/1995 | Imran |
| 5,391,147 A | 2/1995 | Imran et al. |
| 5,395,328 A | 3/1995 | Ockuly et al. |
| 5,395,329 A | 3/1995 | Fleischhacker et al. |
| 5,397,304 A | 3/1995 | Truckai |
| 5,431,168 A | 7/1995 | Webster, Jr. |
| 5,445,148 A | 8/1995 | Jaraczewski et al. |
| 5,474,568 A * | 12/1995 | Scott .................. A61B 17/0469 112/169 |
| 5,478,330 A | 12/1995 | Imran et al. |
| 5,487,385 A | 1/1996 | Avitall |
| 5,487,757 A | 1/1996 | Truckai et al. |
| 5,527,279 A | 6/1996 | Imran |
| 5,531,687 A | 7/1996 | Snoke et al. |
| 5,533,967 A | 7/1996 | Imran |
| 5,545,200 A | 8/1996 | West |
| 5,562,619 A | 10/1996 | Mirarchi et al. |
| 5,582,609 A | 12/1996 | Swanson et al. |
| 5,588,964 A | 12/1996 | Imran et al. |
| 5,611,777 A | 3/1997 | Bowden et al. |
| 5,626,136 A | 5/1997 | Webster, Jr. |
| 5,656,029 A | 8/1997 | Imran et al. |
| 5,656,030 A | 8/1997 | Hunjan et al. |
| 5,755,760 A | 5/1998 | Maguire et al. |
| 5,779,669 A | 7/1998 | Hassaguerre et al. |
| 5,807,249 A | 9/1998 | Qin et al. |
| 5,826,576 A | 10/1998 | West |
| 5,827,272 A | 10/1998 | Breining et al. |
| 5,827,278 A | 10/1998 | Webster |
| 5,836,947 A | 11/1998 | Fleischman et al. |
| 5,842,984 A | 12/1998 | Avitall |
| 5,843,031 A | 12/1998 | Hermann et al. |
| 5,843,076 A | 12/1998 | Webster, Jr. et al. |
| 5,861,024 A | 1/1999 | Rashidi |
| 5,865,800 A | 2/1999 | Mirachi et al. |
| 5,885,278 A | 3/1999 | Fleischman et al. |
| 5,897,529 A | 4/1999 | Ponzi |
| 5,910,129 A | 6/1999 | Koblish et al. |
| 5,916,213 A | 6/1999 | Haissaguerre et al. |
| 5,916,214 A | 6/1999 | Cosi et al. |
| 5,921,924 A | 7/1999 | Avitall |
| 5,931,811 A | 8/1999 | Haissaguerre et al. |
| 5,935,102 A | 8/1999 | Bowden et al. |
| 5,938,616 A * | 8/1999 | Eaton .................. A61B 1/0052 600/446 |
| 5,944,690 A | 8/1999 | Falwell |
| 5,987,344 A | 11/1999 | West |
| 5,993,462 A | 11/1999 | Pomeranz et al. |
| 6,002,955 A | 12/1999 | Willems et al. |
| 6,024,722 A | 2/2000 | Rau et al. |
| 6,027,473 A | 2/2000 | Ponzi |
| 6,033,403 A | 3/2000 | Tu et al. |
| 6,048,329 A | 4/2000 | Thompson et al. |
| 6,059,739 A | 5/2000 | Baumann |
| 6,064,902 A | 5/2000 | Haissaguerre et al. |
| 6,066,125 A | 5/2000 | Webster, Jr. |
| 6,068,629 A | 5/2000 | Haissaguerre et al. |
| 6,071,274 A | 6/2000 | Thompson et al. |
| 6,071,279 A | 6/2000 | Whayne et al. |
| 6,071,282 A | 6/2000 | Fleischman |
| 6,083,222 A | 7/2000 | Klein et al. |
| 6,090,104 A | 7/2000 | Webster, Jr. |
| 6,123,699 A | 9/2000 | Webster, Jr. |
| 6,138,043 A | 10/2000 | Avitall |
| 6,149,663 A | 11/2000 | Stranberg et al. |
| 6,156,034 A | 12/2000 | Cosio et al. |
| 6,169,916 B1 | 1/2001 | West |
| 6,171,277 B1 | 1/2001 | Ponzi |
| 6,178,354 B1 | 1/2001 | Gibson |
| 6,183,435 B1 | 2/2001 | Baunbalough et al. |
| 6,183,463 B1 | 2/2001 | Webster, Jr. |
| 6,198,974 B1 | 3/2001 | Webster, Jr. |
| 6,200,315 B1 | 3/2001 | Gaiser et al. |
| 6,203,507 B1 | 3/2001 | Wadsworth et al. |
| 6,203,525 B1 | 3/2001 | Whayne et al. |
| 6,210,362 B1 | 4/2001 | Ponzi |
| 6,210,407 B1 | 4/2001 | Webster |
| 6,214,002 B1 | 4/2001 | Fleischman et al. |
| 6,221,087 B1 | 4/2001 | Anderson et al. |
| 6,224,587 B1 | 5/2001 | Gibson |
| 6,241,754 B1 | 6/2001 | Swanson et al. |
| 6,308,091 B1 | 10/2001 | Avitall |
| 6,375,654 B1 | 4/2002 | McIntyre |
| 6,430,426 B2 | 8/2002 | Avitall |
| 6,454,758 B1 | 9/2002 | Thompson et al. |
| 6,533,783 B1 | 3/2003 | Tollner |
| 6,582,536 B2 | 6/2003 | Shimda |
| 6,652,506 B2 | 11/2003 | Bowe |
| 6,728,563 B2 | 4/2004 | Rashidi |
| 7,025,759 B2 | 4/2006 | Muller |
| 2002/0032365 A1 | 3/2002 | Hasegawa |
| 2002/0082584 A1 | 6/2002 | Rosenman et al. |
| 2003/0149422 A1 | 8/2003 | Muller |
| 2005/0038333 A1 | 2/2005 | Sra |
| 2006/0142695 A1 | 6/2006 | Knudson |

FOREIGN PATENT DOCUMENTS

| | | |
|---|---|---|
| JP | H05-33736 | 5/1993 |
| JP | H5-229730 | 9/1993 |
| JP | H11-000373 | 1/1999 |
| JP | 3068688 | 5/2000 |
| JP | 2001-275928 | 10/2001 |
| WO | 1994/001162 | 1/1994 |
| WO | 2007002713 | 1/2007 |
| WO | 2007136984 | 11/2007 |

OTHER PUBLICATIONS

Supplementary European Search Report, EP 07761909, dated Apr. 12, 2011.

International Search Report for PCT Application No. PCT/US06/25082, dated Sep. 12, 2007.

International Search Report for PCT Application No. PCT/US2007/068269, dated Dec. 3, 2008.

* cited by examiner

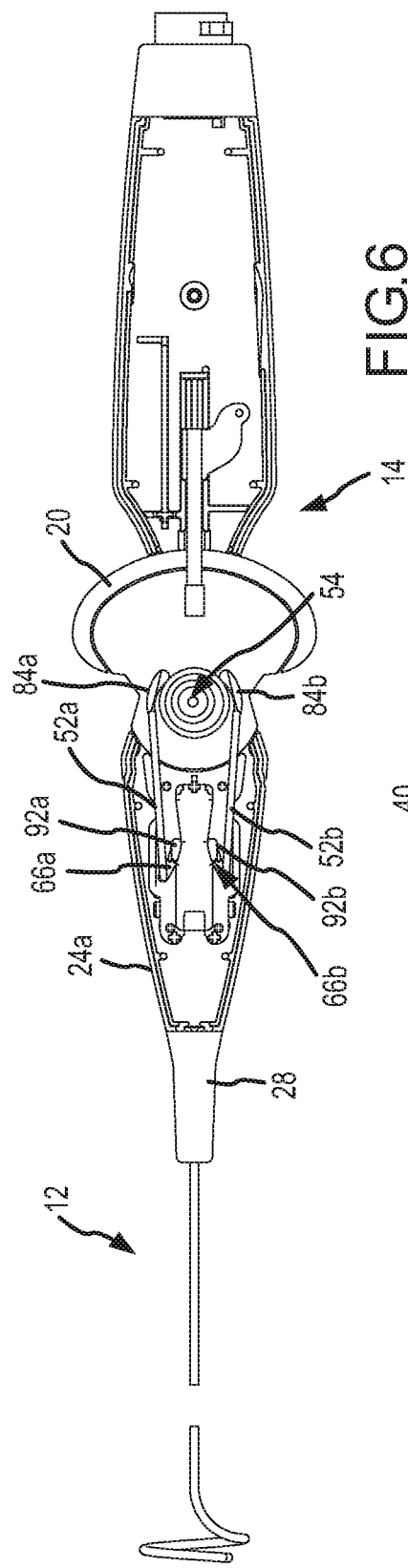
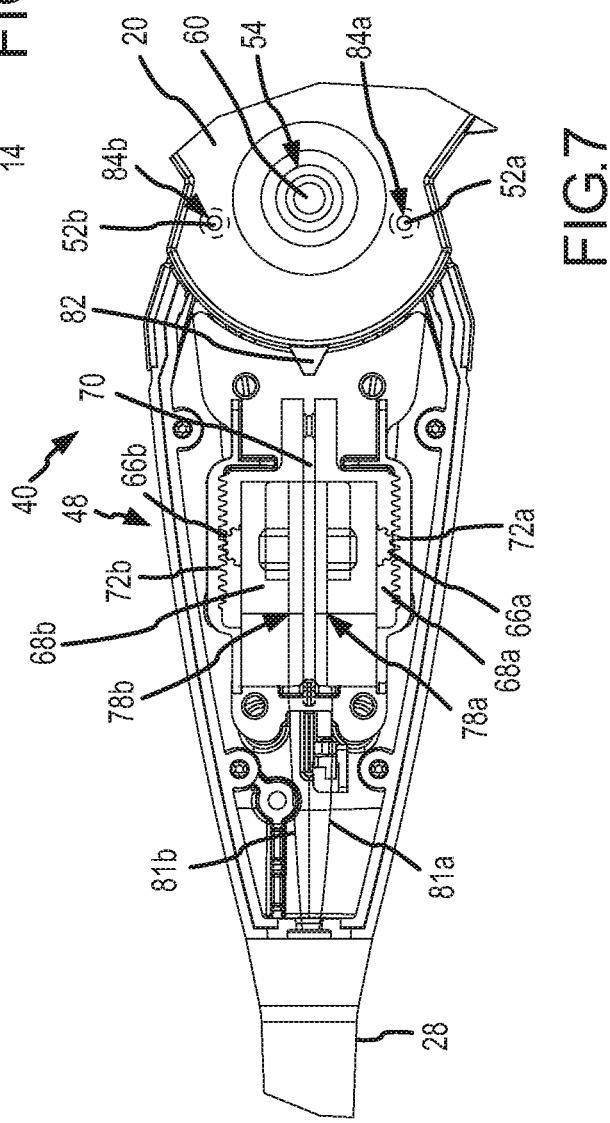

AUTO LOCK FOR CATHETER HANDLE

CROSS-REFERENCE TO RELATED APPLICATION

This application is a continuation application of U.S. patent application Ser. No. 14/311,525, filed 23 Jun. 2014, (the '525 application), which is a continuation of U.S. patent application Ser. No. 11/646,744, filed 27 Dec. 2006 (the '744 application), now U.S. Pat. No. 8,777,929, issued 15 Jul. 2014, which claims the benefit of U.S. provisional application No. 60/801,464, filed 17 May 2006 (the '464 application). The '744 application is also a continuation-in-part of U.S. application Ser. No. 11/170,550, filed 28 Jun. 2005, now U.S. Pat. No. 7,465,288, issued 16 Dec. 2008 (the '550 application), and claims the benefit of U.S. Patent Cooperation Treaty application no. PCT/US2006/025082, filed 27 Jun. 2006 (the '082 application). The '525, the '744, the '464, the '550, and the '082 applications are hereby incorporated by reference as though fully set forth herein.

BACKGROUND OF THE INVENTION a. Field of the Invention

The instant invention relates to catheters and sheaths and methods of using catheters and sheaths. In particular, the instant invention relates to steerable catheter or sheath control handles and methods of manufacturing and using such handles.

b. Background Art

Catheters that have flexible tubular bodies with deflectable distal ends and control handles for controlling distal end deflection are used for many noninvasive medical procedures. For example, catheters having conductive electrodes along the distal ends of their bodies are commonly used for intra-cardiac electrophysiology studies. The distal portion of such a catheter is typically placed into the heart to monitor and/or record the intra-cardiac electrical signals during electrophysiology studies or during intra-cardiac mapping. The orientation or configuration of the catheter distal end is controlled via an actuator located on a handle outside of the body, and the electrodes conduct cardiac electrical signals to appropriate monitoring and recording devices that are operatively connected at the handle of the catheter.

Typically, these catheters include a generally cylindrical electrically nonconductive body. The main body includes a flexible tube constructed from polyurethane, nylon or other electrically non-conductive flexible material. The main body further includes braided steel wires or other non-metallic fibers in its wall as reinforcing elements. Each electrode has a relatively fine electrically conductive wire attached thereto and extending through the main body of the catheter. The conductive wire extends from the distal end to a proximal end where electrical connectors such as plugs or jacks are provided to be plugged into a corresponding socket provided in a recording or monitoring device.

The distal portion of the main body is selectively deformed into a variety of curved configurations using the actuator. The actuator is commonly internally linked to the distal portion of the catheter by at least one actuation wire. Some catheters employ a single actuation wire, which is pulled (i.e., placed in tension) by the actuator in order to cause the distal portion of the main body to deform. Other catheters have at least two actuation wires, where the actuation of one wire (i.e., placing one wire in tension) results in the other wire going slack (i.e., the wire does not carry a compressive load). In such catheters, where the actuation wires are not adapted to carry compressive loads (i.e., the actuation wires are only meant to be placed in tension), the actuation wires are commonly called pull or tension wires.

To deform the distal end of the catheter into a variety of configurations, a more recent catheter design employs a pair of actuation wires that are adapted such that one of the actuation wires carries a compressive force when the other actuation wire carries a tensile force. In such catheters, where the actuation wires are adapted to carry both compressive and tension loads, the actuation wires are commonly called push/pull or tension/compression wires and the corresponding catheter actuators are called push-pull actuators. U.S. Pat. No. 5,861,024 to Rashidi, which issued Jan. 19, 1999, is representative of a push-pull actuator of this type, and the details thereof are incorporated herein by reference.

While many of the existing catheter actuators provide precise operation and good flexibility in movement of the distal portion of the body, the existing actuators often offer a range of distal portion displacement that is less than desirable. In other words, the amount of push/pull of the actuation wires (i.e., the steering travel) is often inadequate for the medical procedure being performed. The inadequacy of the steering travel typically results from the generally limited size of the actuator body, which is usually sized for receipt and manipulation between the thumb and index finger of a user's hand. Accordingly, a need exists to provide an improved actuating assembly for a catheter that increases the amount of steering travel associated with the actuator.

Similarly, once the distal portion has reached a desired position, the physician must either hold the catheter and the actuator in position to keep the distal portion in the desired position, or the handle of the catheter requires the physician to take a conscious step to maintain the distal portion of the catheter at the desired position. Accordingly, a need exists to provide an improved catheter and actuating assembly for a catheter that automatically holds the distal end of the catheter in the desired position. There is also a need in the art for a method of manufacturing and using such a catheter.

BRIEF SUMMARY OF THE INVENTION

The present invention is a catheter actuation handle for deflecting a distal end of a tubular catheter body, the handle including an auto-locking mechanism. The handle includes a grip portion, an actuator, and an auto-locking mechanism. The auto-locking mechanism is adapted to hold a deflected distal end of the catheter in place without input from the operator. As a result, the operator does not need to maintain contact with the buttons to maintain the distal end in a set position once placed there by actuating the actuator.

The auto-locking mechanism can include one or more washers, a bushing, a screw, and a base for receiving the screw. The one or more washers can be the same or different.

The bushing can be constructed of a polymer, a metal, stainless steel, or brass. The screw can be any type of screw, bolt, or connection means, including, preferably, a hex-head screw.

The auto-locking mechanism can further include a tensioning member. The tensioning member can be a Belleville washer or a spring.

The auto-locking mechanism can be a grip activated locking mechanism, or a friction wheel.

The vertical load path of the auto-locking mechanism can exclude the gripping portions or body of the catheter handle.

The present invention also includes a catheter system including a catheter with a catheter shaft with proximal and distal portions, a handle with an actuator and an auto-locking mechanism attached to the proximal portion of the catheter. The handle is adapted to hold the actuator in a position set by an operator. The catheter system can also include a second actuator and a second auto-locking mechanism.

The aspects, features, details, utilities, and advantages of the present invention will be apparent from reading the following description and claims, and from reviewing the accompanying drawings.

BRIEF DESCRIPTION OF THE DRAWINGS

FIG. 6 is a bottom plan view of the handle with the lower grip portion removed to reveal portions of the first and second actuation mechanisms.

FIG. 7 is the same view depicted in FIG. 4, except of a second embodiment of the first actuator.

DETAILED DESCRIPTION OF THE INVENTION

Figure 1:
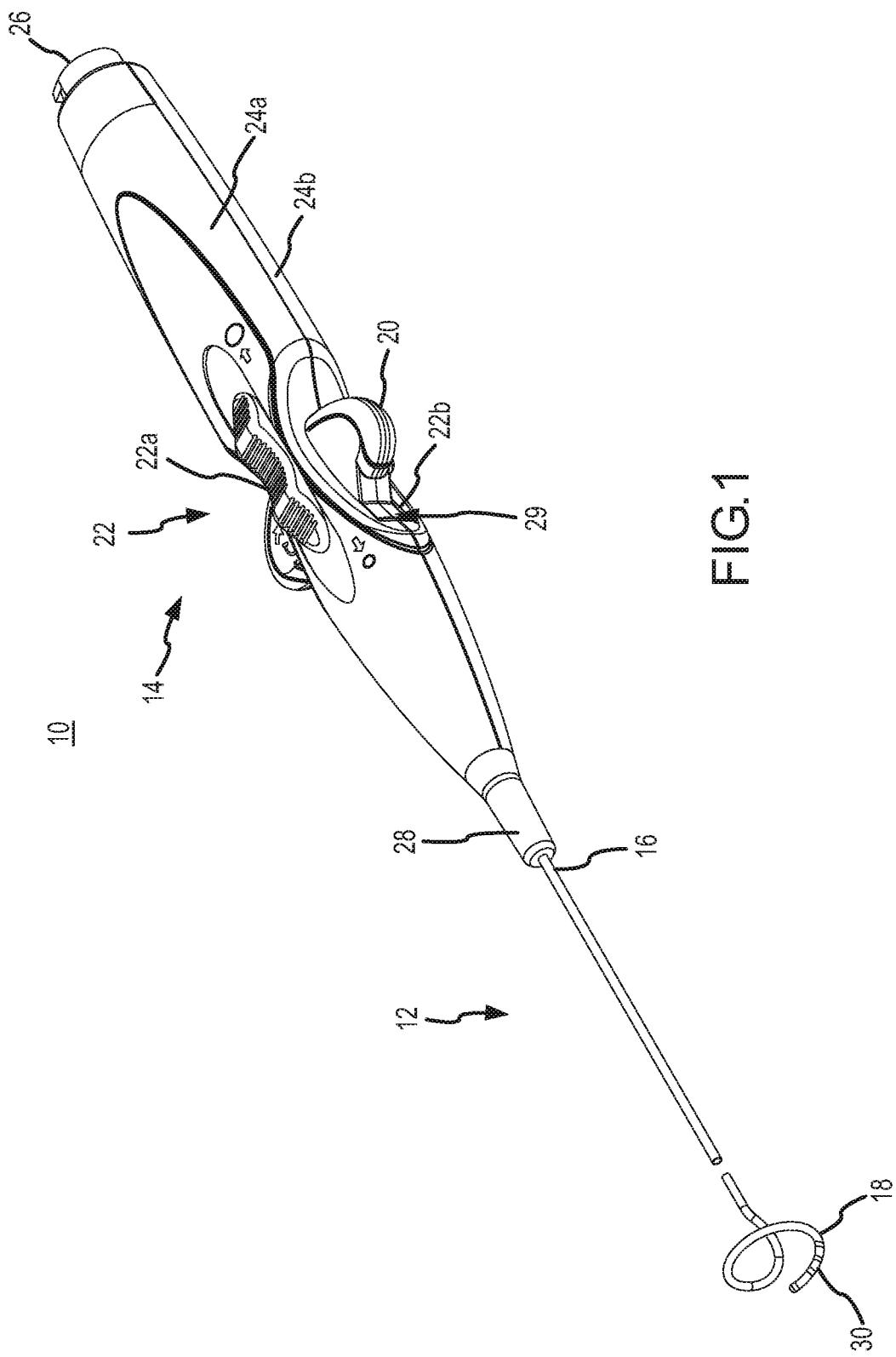
FIG. 1 is an isometric view of the catheter (or sheath) of the present invention.

FIG. 1 is an isometric view of the catheter 10 of the present invention. Throughout this specification, the term catheter is meant to include, without limitation, catheters, sheaths, and similar medical devices. As shown in FIG. 1, the catheter 10 can include an elongated flexible generally cylindrical hollow body 12 and an ergonomically shaped actuation handle 14 coupled to a proximal end 16 of the body 12. The actuation handle 14 is adapted to control the deflection of a deflectable distal end 18 of the body 12.

In one embodiment, as taught in U.S. patent application Ser. No. 11/170,550 to Dudney et al., which was filed on Jun. 28, 2005 and is hereby incorporated in its entirety into this application, the catheter 10 is advantageous for several reasons. First, the actuation handle 14 has a novel rack and pinion actuation mechanism that provides significantly increased steering travel of the distal end 18 of the body 12, as compared to prior art actuation handles. Second, the actuation mechanism is configured such that it does not compress the actuation wires. Third, the actuation mechanism is configured such that the actuation force perceived by a user is minimized and generally constant over the full range of displacement, as compared to prior art actuation mechanisms. Fourth, when the body 12 includes three actuation wires extending through the body 12 from the distal end 18 to the actuation handle 14, the handle has a second actuation mechanism that is configured to actuate the third actuation wire.

As shown in FIG. 1, the actuation handle 14 can include a first actuator 20, upper and lower buttons 22a, 22b of a second actuator, upper and lower grip portions 24a, 24b, an electrical plug 26 at the proximal end of the handle 14, and a strain relief 28 at the distal end of the handle 14. The upper and lower grip portions 24a, 24b define a space 29 that extends laterally through the grip portions 24a, 24b. The first actuator 20 is pivotally coupled to the grip portions 24a, 24b and resides in the space 29. The first actuator 20 may pivotally displace laterally relative to the grip portions 24a, 24b through the space 29. Such pivotal displacement of the first actuator 20 allows a user to bi-directionally deflect the distal end 18 of the body 12.

The upper and lower buttons 22a, 22b of the second actuator 22 are slideably coupled to their respective grip portions 24a, 24b in such a manner that they may slideably displace along their respective grip portions 24a, 24b in a direction that is generally parallel to the longitudinal axis of the handle 14. Such slideable displacement of the buttons 22a, 22b of the second actuator 22 allows a user to deflect the distal end 18 of the body 12 in a third direction. For example, as indicated in FIG. 1, in one embodiment where the distal end 18 forms a loop or lariat, the first actuator 20 causes the distal end 18 to deflect bi-directionally right or left, and the buttons 22a, 22b of the second actuator 22 cause the distal end 18 to increase or decrease the diameter of its loop or lariat. In another embodiment, as taught in U.S. patent application Ser. No. 10/784,511 to Rashidi, which was filed on Feb. 23, 2004 and is hereby incorporated in its entirety into this application, the first actuator 20 causes the distal end 18 to bi-directionally loop and to increase or decrease the extent to which the distal end 18 loops. The buttons 22a, 22b of the second actuator 22 cause the loop or lariat formed by the distal end 18 to nod or deflect.

As illustrated in FIG. 1, the distal end 18 of the body 12 can include a plurality of spaced electrodes 30. Each electrode 30 is connected to a fine electrical conductor wire that extends to the electrical plug 26 through the body 12, the strain relief 28, and the handle 14. The electrical plug 26 is adapted to be connected to a device, such as a recording, monitoring, or RF ablation device. While a variety of material can be used to construct body 12, it is typically constructed of polyurethane, nylon or any suitable electrically non-conductive material. The body 12 serves as at least a portion of the blood contacting segment of the catheter 10 and is vascularly inserted into a patient by methods and means well known in the art.

The actuation wires can be any of the actuation wire types known in the art. They can be pull or tension wires (i.e., the actuation wires are not adapted to support a compressive load). They can also be configured such that the actuation wires are pull/push or tension/compression wires (is., the actuation wires are adapted to support a compressive load). Thus, in the context of the first and second actuation wires, when one actuation wire is placed in tension, the other actuation wire will carry a compressive load. The actuation wires can be formed from a super elastic Nitinol wire or another suitable material. Detailed discussion regarding the configuration of the body 12 and its three actuation wires is provided in the aforementioned incorporated U.S. patent and patent application.

Figure 2:
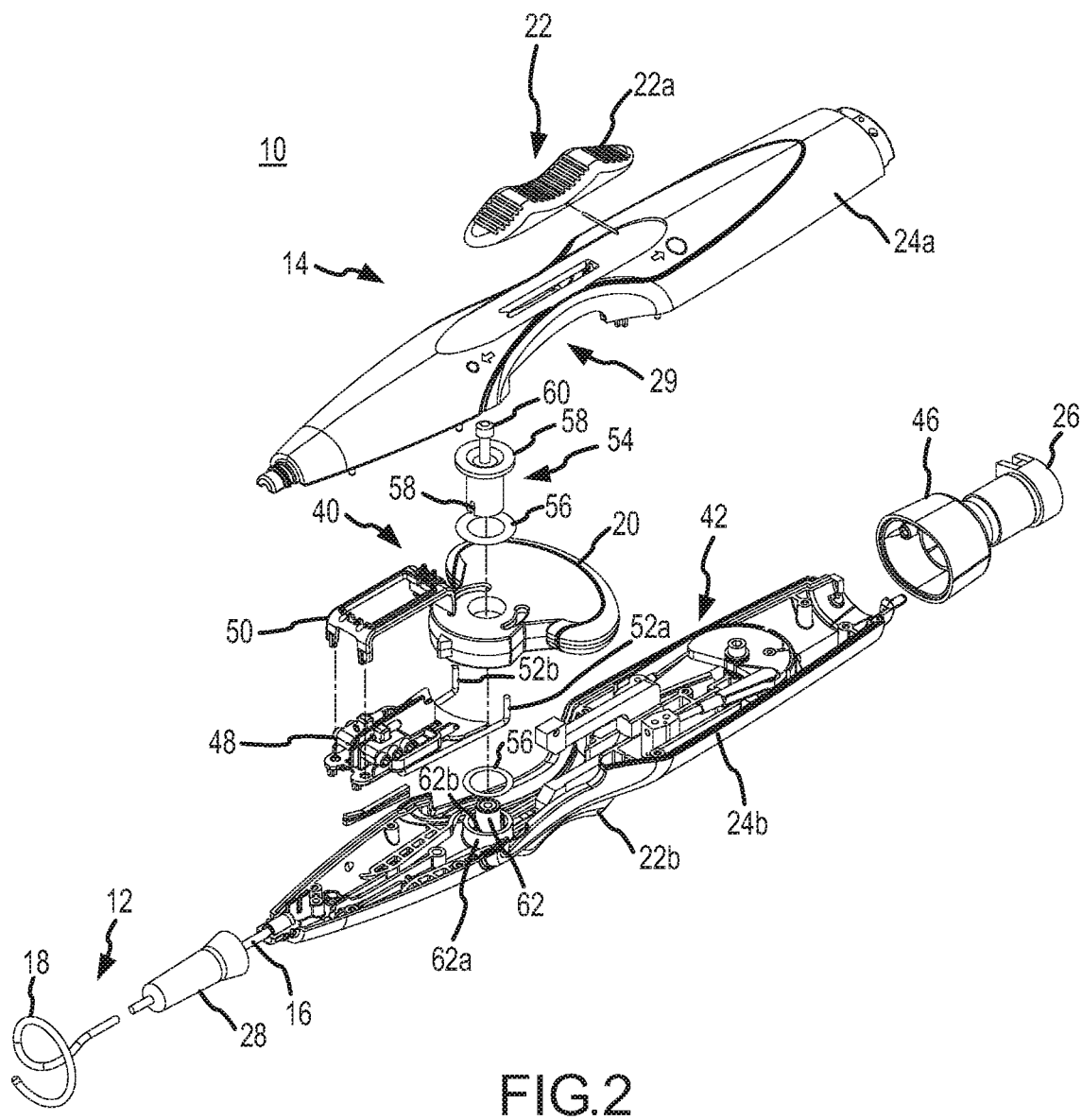
FIG. 2 is an isometric view of the handle with the upper and lower grip portions separated and the first actuation mechanism exploded to better illustrate its various components.

For a detailed discussion of one embodiment of the handle 14 of the subject invention, reference is now made to FIG. 2, which is an isometric view of the handle 14 with the upper and lower grip portions 24a, 24b separated and the first actuation mechanism 40 exploded to better illustrate its various components. As shown in FIG. 2, the grip portions 24a, 24b of the handle 14 are adapted to matingly couple with each other and serve as an enclosure and mounting base for the first and second actuation mechanisms 40, 42 and the auto-locking mechanism, 54. The first actuation mechanism 40 is mounted in a distal portion of the handle 14, and the second actuation mechanism 42 is mounted in a proximal portion of the handle 14. The electrical plug 26 is mounted in a proximal end assembly 46 that serves as the proximal end of the handle 14.

As illustrated in FIG. 2, the first actuation mechanism 40 includes the first actuator 20, a gear assembly 48 with a cover 50, first and second control arms 52a, 52b, and an auto-locking mechanism 54. The auto-locking mechanism 54 can assume any one of numerous formats, but is adapted to hold the distal end of the catheter in place without conscious and/or actual input from the operator, depending on the embodiment.

In catheter operation, the operator will manipulate one or more of the first or second actuators 20, 22, causing the distal end 18 to deflect from the original position as manufactured, or its zero position. Typically, the distal end 18 of the catheter is naturally biased to return toward its zero position, and accordingly exerts a pressure on the first or second actuators 20, 22 through the actuation wires to return towards the zero position. In prior art devices this pressure must be counteracted by the operator, either by holding the actuator(s) in place, or by manually setting a locking mechanism before or during the procedure. In the present invention, the auto-locking mechanism automatically retains the distal end in the deflected state set by the operator with no input from the operator, freeing the operator to perform other tasks.

As illustrated in FIG. 2, the auto-locking mechanism 54 pivotally couples the first actuator 20 to the lower grip portion 24b and can include one or more washers 56, a bushing 58 and a screw 60, e.g., a hex-head screw, for attaching the auto-locking mechanism 54 as an integral unit to a pivot base 62 on the lower grip portion 24b. As shown in FIG. 2, each washer 56 can be a different size.

Figure 3:
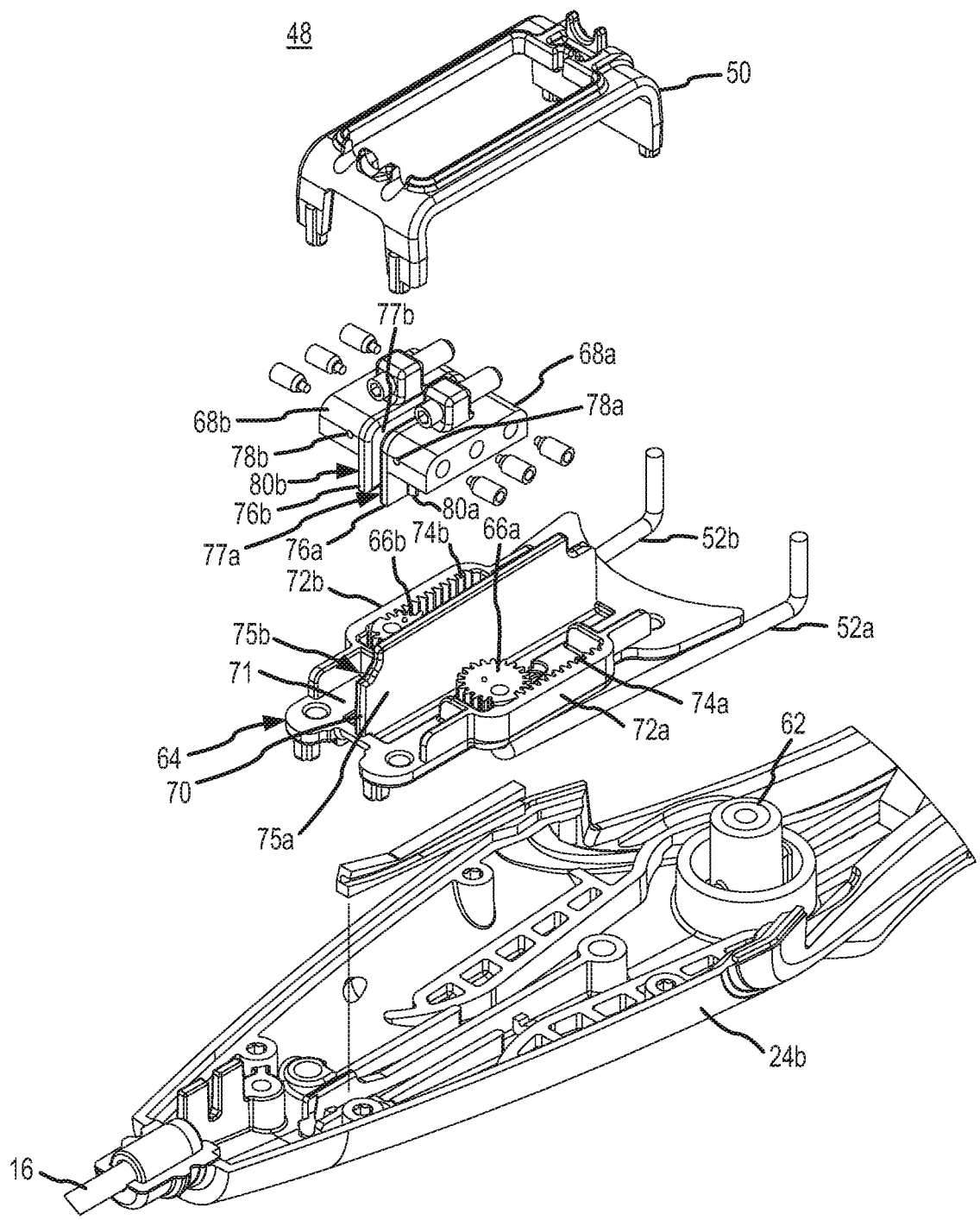
FIG. 3 is an exploded isometric view of the gear assembly.

For a detailed discussion of the gear assembly 48, reference is now made to FIG. 3, which is an exploded isometric view of the gear assembly 48. As shown in FIG. 3, the gear assembly 48 includes a frame 64, first and second pinion gears 66a, 66b, first and second wire blocks 68a, 68b, and the cover 50. The frame 64 includes a face plate 70, a base or floor 71, and first and second stationary gear racks 72a, 72b. The first and second stationary gear racks 72a, 72b are fixed to the lateral sides of the base 71 of the frame 64 and oriented such that their respective teeth sides 74a, 74b face each other and are generally parallel to the longitudinal centerline of the frame 64. The face plate 70 is aligned with the longitudinal centerline of the frame 64, positioned between the two stationary gear racks 72a, 72b, and generally perpendicular to the base 71 of the frame 64. Each vertical side or face 75a, 75b of the faceplate 70 is generally planar.

As indicated in FIG. 3, each wire block 68a, 68b includes a movable gear rack 76a, 76b, a generally planar vertically oriented face 77a, 77b, and a hole 78a, 78b. Each movable gear rack 76a, 76b extends downwardly from its respective wire block 68a, 68b and has teeth 80a, 80b on one side and a generally planar vertical face 77a, 77b on the other. The moveable gear racks 76a, 76b are oriented such that they are generally parallel to each other, their teeth 80a, 80b face away from each other, and their planar faces 77a, 77b face each other in a generally parallel arrangement.

Each hole 78a, 78b is adapted to receive a proximal end of one of the first and second actuation wires. For example, as illustrated in FIG. 4, which is a top plan view of a first embodiment of the first actuation mechanism 40 mounted in the proximal portion of the lower grip portion 24b, the first and second actuation wires 81a, 81b are received in their respective holes 78a, 78b upon exiting the proximal end 16 of the body 12.

Figure 4:
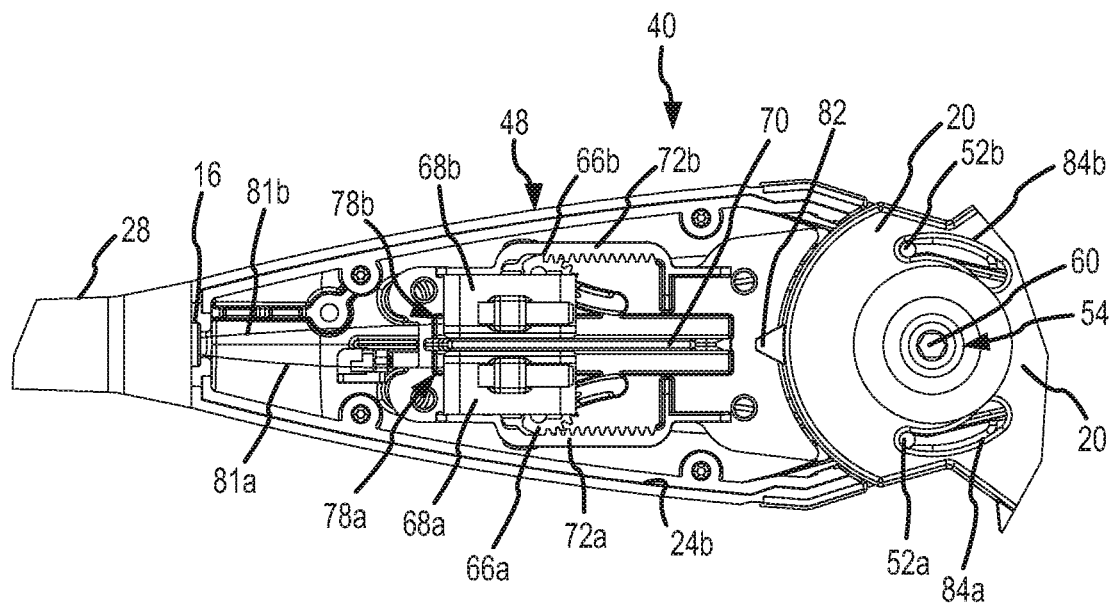
FIG. 4 is a top plan view of a first embodiment of the first actuation mechanism mounted in the proximal portion of the lower grip portion, wherein the first and second actuation wires are received in their respective holes in the wire blocks.

As shown in FIG. 4, the actuator 20 is pivotally mounted to the lower grip portion 24b via the pivot assembly 54. The first actuation assembly 40 is located distal to the actuator 20 and proximal to the to the strain relief 28. In one embodiment, the first actuator 20 includes a position indicator point 82 on its most distal edge and first and second openings 84a, 84b that are located on opposite lateral sides of the actuator 20.

As indicated in FIG. 4, a proximal end of a control arm 52a, 52b resides in each opening 84a, 84b. In a first embodiment of the first actuation mechanism 48, as depicted in FIG. 4, the openings 84a, 84b are arcuate slots 84a, 84b that are substantially longer in length than the diameter of the control arm 52a, 52b.

Figure 5:
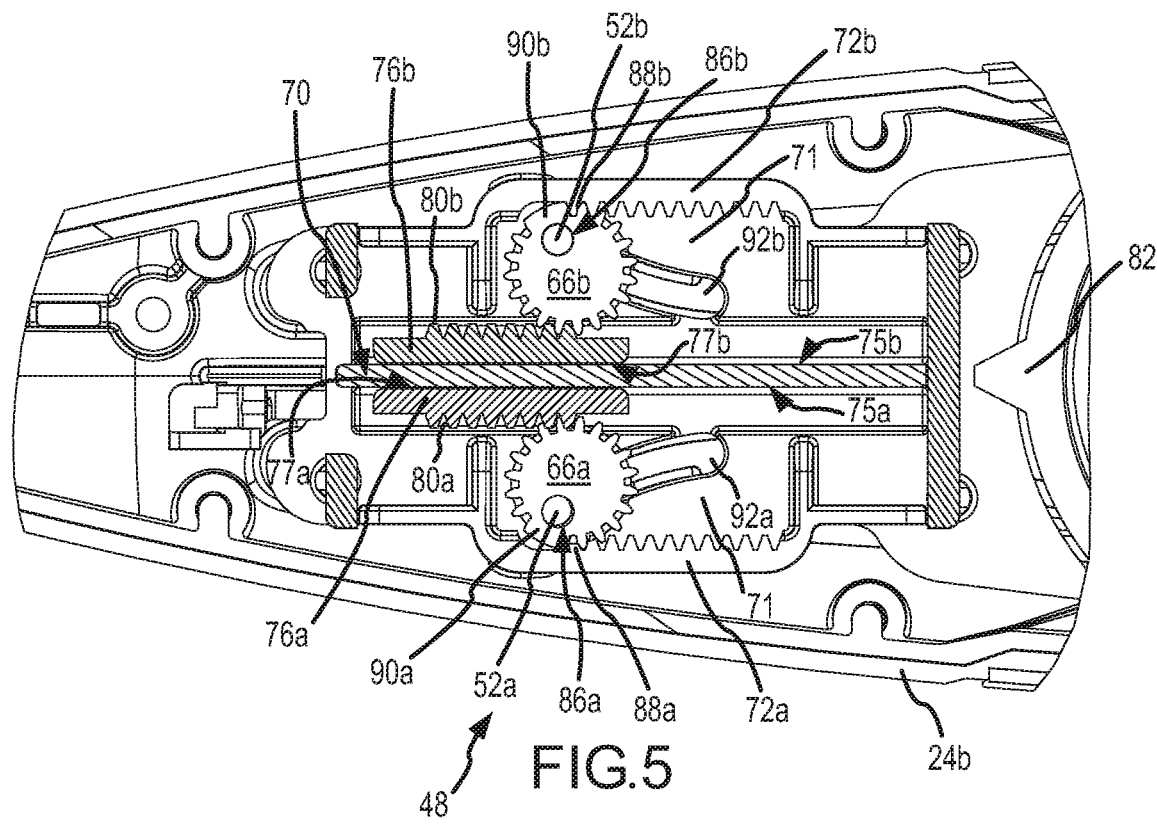
FIG. 5 is an enlarged plan view of the gear assembly with the top portions of the wire blocks removed to better illustrate the gearing arrangement.

As illustrated in FIG. 5, which is an enlarged plan view of the gear assembly 48 with the top portions of the wire blocks 68a, 68b removed to better illustrate the gearing arrangement, a distal end of a control arm 52a, 52b resides in a hole 86a, 86b in each pinion gear 66a, 66b. In one embodiment, each hole 86a, 86b is positioned at the axial center of its respective pinion gear 66a, 66b. In another embodiment, as depicted in FIG. 5, each hole 86a, 86b is offset from the axial center of its respective pinion gear 66a, 66b.

As shown in FIG. 6, which is a bottom plan view of the handle 14 with the lower grip portion 24b removed to reveal portions of the first and second actuation mechanisms 40, 42, each control arm 52a, 52b extends between its respective points of connection with a hole 86a, 86b of a pinion 66a, 66b and an opening 84a, 84b in the first actuator 20. Thus, as will be understood from FIGS. 4-6, the control arms 52a, 52b serve as linkages to transmit the motion of the first actuator 20 to the pinions 66a, 66b.

As illustrated in FIG. 5, each pinion gear 66a, 66b is positioned between, and engaged with, a stationary gear rack 72a, 72b and a moveable gear rack 76a, 76b. A generally planar back 77a, 77b of each moveable gear rack 76a, 76b slideably abuts against a respective generally planar face 75a, 75b of the faceplate 70.

As shown in FIG. 5, in one embodiment, where the hole 86a, 86b in each pinion 66a, 66b is offset from the pinion's axial center, when the pinion 66a, 66b is positioned at the most distal end of the stationary gear rack 72, 72b, the hole 86a, 86b will be located immediately adjacent, and slightly distal to, the most distal tooth 88a, 88b of the respective stationary gear rack 72a, 72b. In one embodiment, to prevent the pinions 66a, 66b from over traveling relative to the gear racks 72a, 72b, 76a, 76b, a blank toothless section 90a, 90b exists along the circumference of each pinion 66a, 66b next to the pinion's hole 86a, 86b.

As shown in FIGS. 5 and 6, an arcuate slot 92a, 92b exists between each pair of gear racks 72a, 72b, 76a, 76b in a base or floor portion 71 of the frame 64. Each arcuate slot 92a, 92b serves as a pathway through which the distal portion of each control arm 52a, 52b may pass as the respective pinion gear 66a, 66b displaces along the stationary gear rack 72a, 72b. The arcuate configuration of the arcuate slots 92a, 92b allows the distal parts of each control arm 52a, 52b to follow the sinusoidal displacement of the holes 86a, 86b when the pinions 66a, 66b displace along the stationary gear racks 72a, 72b.

Because the holes 86a, 86b are offset from the axial centers of the pinions 66a, 66b, a mechanical advantage is created as compared to a configuration where the holes 86a, 86b are centered at the axial centers of the pinions 66a, 66b. The mechanical advantage results in an actuation force, as perceived by a user, that is less than and more constant than the actuation forces required to operate prior art catheters.

The operation of the first embodiment of the first actuation mechanism 40, wherein the each opening 84a, 84b is an arcuate slot 84a, 84b, will now be described while referencing FIGS. 4-6. As indicated in FIGS. 4-6, when the first actuation mechanism 40 is in a neutral pivotal position (i.e., when the wire blocks 68a, 68b are both in their most proximal positions and the position indicator point 82 is facing distally and is generally aligned with the longitudinal centerline of the lower grip portion 24b, as depicted in FIG. 4), the proximal end of each control arm 52a, 52b is in the most distal portion of its respective arcuate slot 84a, 84b. This configuration of the first embodiment of the first actuation mechanism 40 is advantageous where the actuation wires 81a, 81b are tension or pull type actuation wires. More specifically, it is advantageous where the actuation wires 81a, 81b are only to be placed in tension and never to be compressed, thereby avoiding buckling of the actuation wires 81a, 81b.

For example, as can be understood from FIGS. 4-6, when the first actuator 20 is pivoted in a first direction (e.g., counterclockwise FIG. 4), the proximal end of the first control arm 52a is engaged by the distal end of the first arcuate slot 84a and the first control arm 52a is pulled proximally. This causes the distal end of the first control arm 52a to cause the first pinion gear 66a to displace proximally along the corresponding stationary gear rack 72a. The rotation of the first pinion gear 66a causes the corresponding moveable gear rack 76a to be driven proximally. As can be understood from FIG. 4, this causes the corresponding wire block 68a to place the first actuation wire 81a in tension as the wire block 68a proximally displaces.

While pivoting the actuator 20 in the first direction causes the first wire block 68a to act on the first actuation wire 81a, such a movement, generally speaking, has no impact on the second wire block 68b or the second actuation wire 81b. This is because a counter clockwise rotation of the actuator 20 simply causes the second arcuate slot 84b to slide along the proximal end of the control arm 52b without the proximal end of the second arcuate slot 84b encountering the proximal end of the control arm 52b. As a result, the first actuator 20 does not distally drive the second control arm 52b and the second wire block 68b is not caused to distally displace. Accordingly, the second actuation wire 81b is not placed in tension or compression when the actuator 20 is pivoted in the first direction (i.e., counterclockwise). In other words, the second actuation wire 81b is allowed to relax and move freely.

In one embodiment, when the actuator 20 is pivoted back to the neutral pivotal position depicted in FIG. 4, the proximal end of the first arcuate slot 84a does not encounter the proximal end of the first control arm 52a. As a result, the first actuator 20 does not drive the first wire block 68a and its corresponding actuation wire 52a distally back into the neutral position. Instead, the tension that the deflected distal end 18 exerts on the first actuation wire 52a causes the wire 52a and its corresponding block 52a to return to the neutral position.

Continuing the example, as can be understood from FIGS. 4-6, when the first actuator 20 is pivoted in a second direction (is., clockwise in FIG. 4), the proximal end of the second control arm 52b is engaged by the distal end of the second arcuate slot 84b and the second control arm 52b is pulled proximally. This causes the distal end of the second control arm 52b to cause the second pinion gear 66b to displace proximally along the corresponding stationary gear rack 72b. The rotation of the second pinion gear 66b causes the corresponding moveable gear rack 76b to be driven proximally. As can be understood from FIG. 4, this causes the corresponding wire block 68b to place the second actuation wire 81b in tension as the wire block 68b proximally displaces.

While pivoting the actuator 20 in the second direction causes the second wire block 68b to act on the second actuation wire 81b, such a movement, generally speaking, has no impact on the first wire block 68a or the first actuation wire 81a. This is because a clockwise rotation of the actuator 20 simply causes the first arcuate slot 84a to slide along the proximal end of the control arm 52a without the proximal end of the first arcuate slot 84a encountering the proximal end of the control arm 52a. As a result, the first actuator 20 does not distally drive the first control arm 52a and the first wire block 68a is not caused to distally displace. Accordingly, the first actuation wire 81a is not placed in tension or compression when the actuator 20 is pivoted in the second direction (i.e., clockwise). In other words, the first actuation wire 81a is allowed to relax and move freely.

In one embodiment, when the actuator 20 is pivoted back to the neutral pivotal position depicted in FIG. 4, the proximal end of the second arcuate slot 84b does not encounter the proximal end of the second control arm 52b. As a result, the first actuator 20 does not drive the second wire block 68b and its corresponding actuation wire 52b distally back into the neutral position. Instead, the tension that the deflected distal end 18 exerts on the second actuation wire 52b causes the wire 52b and its corresponding block 52b to return to the neutral position.

As can be understood from FIGS. 4 and 5, because of the gearing arrangement, the proximal linear displacement of a moveable gear rack 76a, 76b and, as a result, its corresponding actuation wire 81a, 81b is generally twice the proximal linear displacement of the corresponding pinion gear 66a, 66b. This is because the proximal displacement of a moveable gear rack 76,76b is the sum of a pinion gear's linear proximal displacement along a stationary gear rack 72a, 72b plus the pinion gear's rotational displacement.

Figure 8:
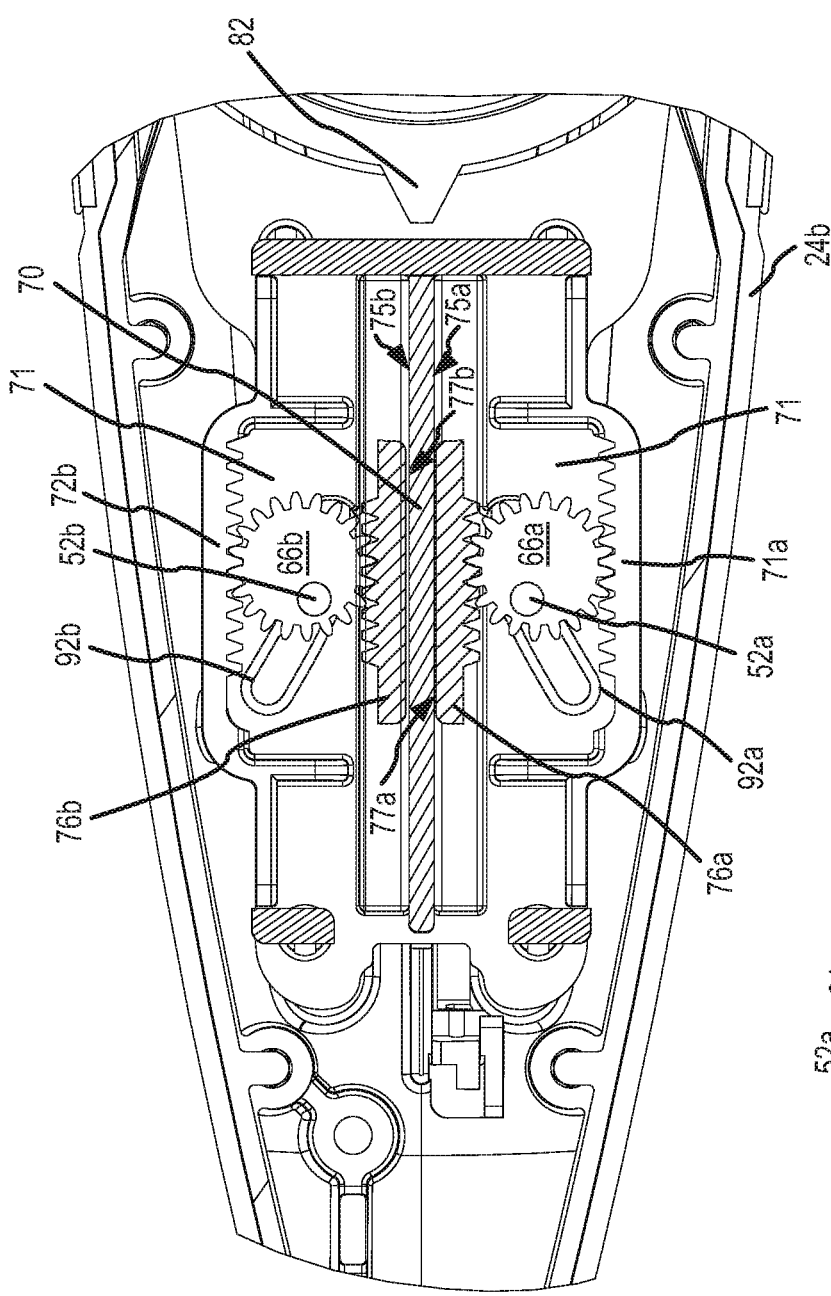
FIG. 8 is the same view depicted in FIG. 5, except of the second embodiment of the first actuator.
Figure 9:
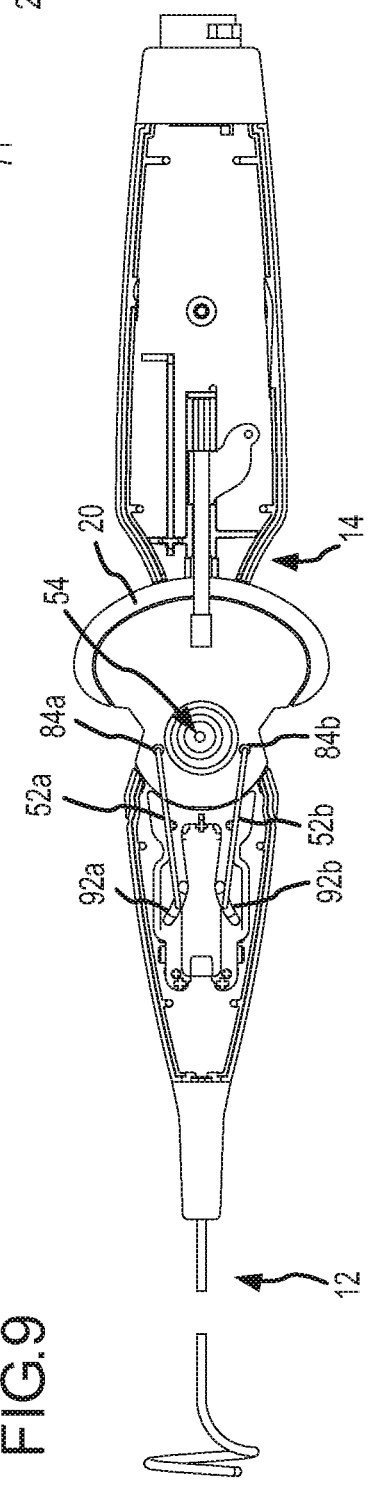
FIG. 9 is the same view depicted in FIG. 6, except of the second embodiment of the first actuator.

For a discussion of a second embodiment of the first actuation mechanism 40, reference is now made to FIGS. 7-9. FIGS. 7-9 are, respectively, the same views depicted in FIGS. 4-6, except of the second embodiment of the first actuation mechanism 40. Generally speaking, the features of the first and second embodiments of the first actuation mechanism 40 are the same, except as provided in the following discussion.

As shown in FIG. 7, unlike the arcuate slots 84a, 84b of the first embodiment of the actuation mechanism 40 (as discussed in reference to FIGS. 4-6), the openings 84a, 84b of the second embodiment are circular holes 84a, 84b with diameters generally equal to the diameter of the control arms 52a, 52b. As indicated in FIG. 7, a proximal end of a control arm 52a, 52b resides in each circular opening 84a, 84b.

As can be understood from FIGS. 7-9, in the second embodiment of the actuation mechanism 40, when the first actuation mechanism 40 is in a neutral pivotal position (i.e., the position indicator point 82 is facing distally and generally aligned with the longitudinal centerline of the lower grip portion 24b, as depicted in FIG. 7), each pinion 66a, 66b is positioned approximately midway along both of the lengths of its respective stationary gear rack 72a, 72b and moveable gear rack 76a, 76b. This arrangement allows the control arms 52a, 52b to oppositely and equally move relative to each other when the actuator 20 is pivoted. This movement is brought about in the second embodiment of the first actuation mechanism 40 because, unlike the arcuate slots 84a, 84b of the first embodiment, the circular openings 84a, 84b of the second embodiment prevent displacement between the proximal ends of the control arms 52a, 52b and the actuator 20. The configuration of the second embodiment of the first actuation mechanism 40 is advantageous where the actuation wires 81a, 81b are pull/push or tension/compression type actuation wires.

For example, as can be understood from FIGS. 7-9, when the first actuator 20 is pivoted in a first direction (e.g., counterclockwise in FIG. 7), the proximal end of the first control arm 52a is pulled proximally by the first circular opening 84a, and the proximal end of the second control arm 52b is pushed distally by the second circular opening 84b. Accordingly, the distal end of the first control arm 52a pulls the first pinion gear 66a proximally along its corresponding stationary gear rack 72a, and the distal end of the second control arm 52b pushes the second pinion gear 66b distally along its corresponding stationary gear rack 72b. The rotation of the first pinion gear 66a proximally drives its corresponding moveable gear rack 76a, and the rotation of the second pinion gear 66b distally drives its corresponding moveable gear rack 76b. As can be understood from FIG. 7, this causes the first wire block 68a to place the first actuation wire 81a in tension as the wire block 68a proximally displaces. Also, this causes the second wire block 68b to push (i.e., compress) the second actuation wire 81b distally as the second wire block 68b distally displaces.

As can be understood from FIGS. 7-9, pivoting the first actuator 20 in a second direction (i.e., clockwise) reverses the movement of the control arms 52a, 52b. Accordingly, the second wire block 68b moves proximally (i.e., the second actuation wire 81b is placed into tension), and first wire block 68a moves distally (i.e., the first actuation wire 81a is compressed or released).

Figure 10:
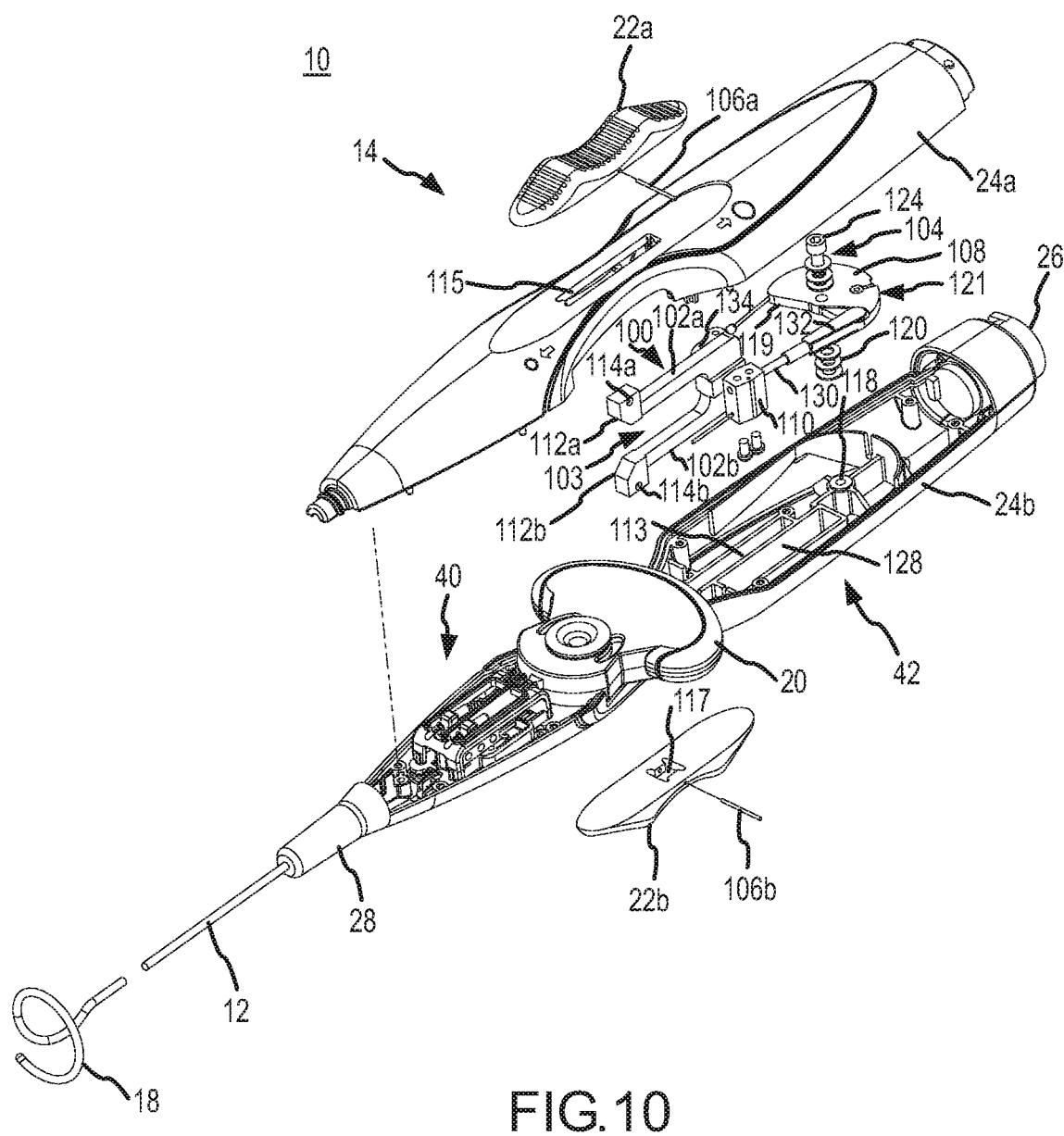
FIG. 10 is an isometric view of the handle with the upper and lower grip portions separated and the second actuation mechanism exploded to better illustrate its various components.

For a detailed discussion of one embodiment of the second actuation mechanism 42, reference is now made to FIG. 10, which is an isometric view of the handle 14 with the upper and lower grip portions 24a, 24b separated and the second actuation mechanism 42 exploded to better illustrate its various components. As shown in FIG. 10, the second actuation mechanism 42 is mounted in a proximal portion of the handle 14 and includes a second actuator 100 with upper and lower arms 102a, 102b, the upper and lower buttons 22a, 22b of the second actuator 100, a pivot assembly 104, upper and lower pins 106a, 106b, a lever 108, and a slide block 110.

As illustrated in FIG. 10, the actuation handle 14 can include a second actuation mechanism 22 with upper and lower buttons 22a, 22b. The second actuation mechanism includes a second actuator 100 that is generally U-shaped. The second actuator's arms 102a, 102b are generally vertically aligned and offset from each other in a parallel arrangement to form a gap 103 through which the proximal portion of the first actuator 20 displaces. The lower arm 102b slideably resides in a longitudinal slot or groove 113 in the lower grip portion 24b. Similarly, the upper arm 102a slideably resides in a longitudinal slot or groove in the upper grip portion 24a.

As shown in FIG. 10, each arm 102a, 102b includes a head 112a, 112b with a pinhole 114a, 114b for receiving a pin 106a, 106b. The upper head 112a extends through a longitudinal slot 115 in the upper grip portion 24a to couple to the upper button 22a. Similarly, the lower head 112b extends through a longitudinal slot in the lower grip portion 24b to couple to the lower button 22b. The lower head 112b resides in a seat 117 in the lower button 22b and is coupled thereto via the pin 106b. Likewise, the upper head 112a resides in a seat in the upper button 22a and is coupled thereto via the pin 106a. Because each button 22a, 22b is coupled to an arm 102a, 102b of the second actuator 100, the buttons 22a, 22b are slaved together.

As indicated in FIG. 10, the heads 112a, 112b are slideably displaceable within their respective longitudinal slots 115. Thus, when a user slides the buttons 22a, 22b longitudinally relative to the grip portions 24a, 24b to actuate the second actuation assembly 42, the arms 102a, 102b and heads 112a, 112b slideably displace in their respective slots 113, 115.

As shown in FIG. 10, the lever 108 is pivotally coupled to a pivot base 118 in the lower grip portion 24b via the pivot assembly 104. The pivot assembly 104 includes a series of washers 120 (including a Belleville spring washer to compensate for compression set or material creep during the catheter's shelf life), and a hex-head screw 124 for securing the pivot assembly 104 to the pivot base 118 as one integral unit. When the hex-head screw 124 is properly tightened, the pivot assembly 104 is configured such that it acts as an auto-locking mechanism 54 by providing a tension drag feature that holds the lever 108 in place although the user has released the buttons 22a, 22b. As a result, the user does not need to maintain contact with the buttons 22a, 22b to maintain the distal end 18 in a set position once placed there by the user actuating the second actuation mechanism 42.

As illustrated in FIG. 10, in one embodiment, the lever 108 is generally semicircular such that it has a generally linear edge 119 and a generally arcuate edge 121 extending between the first and second ends of the linear edge 119. The linear edge 119 is adjacent the pivot assembly 104 and faces generally distally. In one embodiment, the radius of the arcuate edge 121 is generally equal to the distance between the arcuate edge 121 and the axis of the pivot assembly 104. The arcuate edge 121 faces generally proximally.

Figure 11:
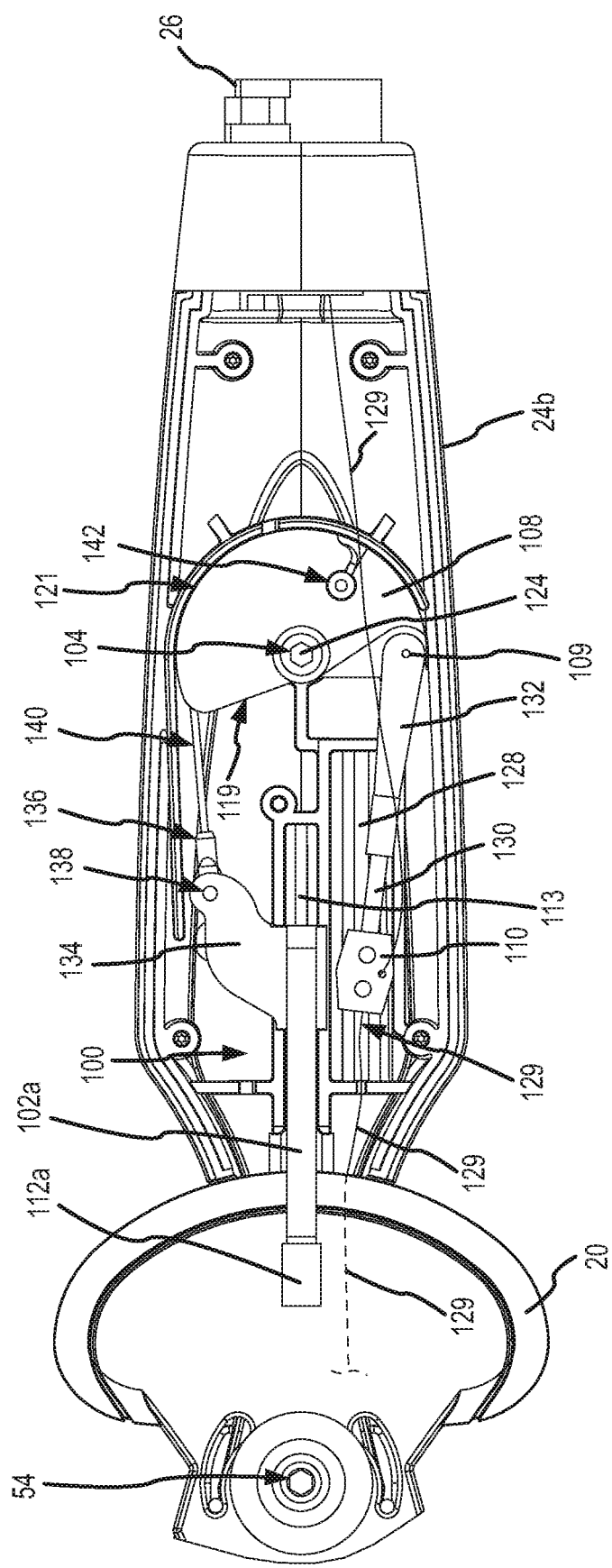
FIG. 11 is a top plan view of the second actuation mechanism mounted in the lower grip portion with the upper grip portion removed.

For further discussion of the components of the second actuation mechanism 42, reference is now made to FIG. 11, which is a top plan view of the second actuation mechanism 42 mounted in the lower grip portion 24b with the upper grip portion 24a removed. As indicated in FIG. 11, a bottom end of the slide block 110 is slideably received in a lower groove or slot 128 in the lower grip portion 24b. Similarly, a top end of the slide block 110 is slideably received in an upper groove or slot in the upper grip portion 24a. The slots 128 are generally parallel to the longitudinal axis of the handle 14.

As illustrated in FIG. 11, a third actuation wire 129 extends from the distal end 18 of the body 12 and into the handle 14 to couple the slide block 110. In one embodiment, the third actuation wire 129 also serves as an electrical wire leading from one or more electrodes 30 in the distal tip 18 to the electrical plug 26 in the proximal end of the handle 14. In doing so, the third actuation wire 129 passes through, and couples to, the slide block 110.

As shown in FIG. 11, a threaded rod 130 extends between a proximal side of the slide block 110 and a clevis 132 pivotally attached to a first end of the lever 108 via a pin 109. The threads on the threaded rod 130 allow the distance between the clevis 132 and the slide block 110 to be adjusted. Thus, the initial actuation wire position relative to the lever 108 can be adjusted via the threaded rod 130.

As indicated in FIG. 11, an arm 134 extends from the proximal end of the second actuator 100 in a direction opposite from the slide block 110. A link 136 is pivotally coupled to an end of the arm 134 via a pin 138. A cable 140 is coupled to the link 136 and extends to and around the arcuate side 121 of the lever 108 to couple to the lever 108 via an attachment feature 142 (e.g., a screw, bolt, pin, etc.). The arcuate side 121 of the lever 108 is grooved or slotted to receive the cable 140. The cable 140 and arcuate side 121 of the lever 108 operate together like a belt and pulley such that a moment arm between the cable 140 and the pivotable lever 108 remains constant as the lever 108 pivots.

As can be understood from FIG. 11, when actuating the third actuation wire 129 to cause the distal end 18 of the body 12 to deflect, a user displaces a button 22a, 22b distally, which causes the U-shaped second actuator 100 to displace distally. As a result, the arm 134 pulls the cable 140 distally, thereby causing the lever 108 to pivot in a counterclockwise direction about the pivot assembly 104. This pivoting movement causes the clevis 132 to pull the slide block 110 in a proximal direction. The proximal movement of the slide block 110 places the third actuation wire 129 into tension (i.e., it pulls the third actuation wire 129), which causes the distal end 18 of the body 12 to deflect.

Increasingly deflecting the distal end of the body 12 requires an increasing force. Thus, during the initial stages of distal end deflection of the body 12, the force needed to pull the third actuation wire 129 is lower than at the final stages of distal end deflection. The increasing force needed to further increase the deflection of the distal end of the body 12 is addressed by the configuration between the clevis 132 and the lever 108. Specifically, the configuration between the clevis 132 and the lever 108 is such that the moment arm changes as the lever 108 pivots.

The moment arm length between the clevis 132 and the pivot assembly 104 of the lever 108 is greatest during the initial stages of distal tip deflection (i.e., when the pin 109 is at its most distal position). Because of the configuration between the clevis 132 and the lever 108, the length of the moment arm decreases as the distal end 18 is increasingly deflected (i.e., the pin 109 moves proximally). Consequently, the mechanical advantage at the buttons 22a, 22b is the least when the actuation wire tension is low (i.e., during the initial stages of distal end deflection) and the most when the actuation wire tension is high (i.e., during the last stages of distal end deflection approaching full deflection).

As can be understood from FIG. 11, to allow the deflected distal end 18 to return to its non-deflected configuration, a user proximally displaces a button 22a, 22b, which causes the U-shaped second actuator 100 to proximally displace. This provides slack in the cable 140, which allows the lever 108 to pivot clockwise as the spring force stored in the deflected distal end 18 acts to distally pull the third actuation wire 129 and, as a result, the slide block 110 as the distal end 18 springs back into a non-deflected configuration.

In use, the body 12 of the catheter 10 is inserted into the patient in a manner well known in the art. An operator grasps the handle 14 and manipulates the first actuator 20 between his thumb and finger. Advantageously, the first actuator 20 protrudes from each side of the handle 14 to allow for such ease of movement and manipulation. The first actuator 20 is moved relative to the handle 14, which causes the first and second actuation wires 78a, 78b to be displaced via the first actuation mechanism 40. As a result, the distal end 18 of the body 12 deflects.

To deflect the distal end 18 of the body 12 in another manner, the user distally slides the buttons 22a, 22b with a thumb or finger. This causes the third action wire 129 to displace via the second actuation mechanism 42. As a result, the distal end 18 of the body 12 deflects in manner different from the deflection brought about by the actuation of the first actuation mechanism 40. For example, the displacement of the third action wire 129 may bring about a deflection of the distal end into any curvilinear shape, such as a loop, a spiral, or into an s shape. In addition, the distal end may be preformed into any curvilinear shape, including a loop, a spiral, or an s-shape, and the displacement of the third action wire may bring about a widening or narrowing of the curvilinear shape. Likewise, the first and second action wires 78a, 78b can bring about a deflection in a first plane, and the third action wire 129 may bring about a deflection in a second plane, e.g., a plane perpendicular to the first plane.

In another embodiment, as illustrated in FIG. 2, an auto-locking mechanism 54 pivotally couples the first actuator 20 to the lower grip portion 24b and can include one or more washers 56, a bushing 58 and a screw 60, e.g., a hex-head screw, for attaching the auto-locking mechanism 54 as an integral unit to a pivot base 62 on the lower grip portion 24b. As shown in FIG. 2, each washer 56 can be the same or different.

As will be appreciated by one of ordinary skill in the art, the bushing 58 can be constructed of any of a number of materials, including commonly available polymers, e.g., PEEK, polysulfone, etc., metals, e.g., stainless steel, brass, etc., or other materials. The washers 56 can be any commonly available form, including flat washers or wave washers and constructed of stainless steel, brass, or a polymeric material. The screw 60 can be any type of screw, bolt, or connection means, including, preferably, a hex-head screw. The pivot base 62 can be constructed of the same or different materials as the lower grip portion 24b. The pivot base 62 can be constructed integrally with the lower grip portion 24b, or it can be a separate piece that is glued, welded or otherwise attached to lower grip portion 24b.

Figure 12:
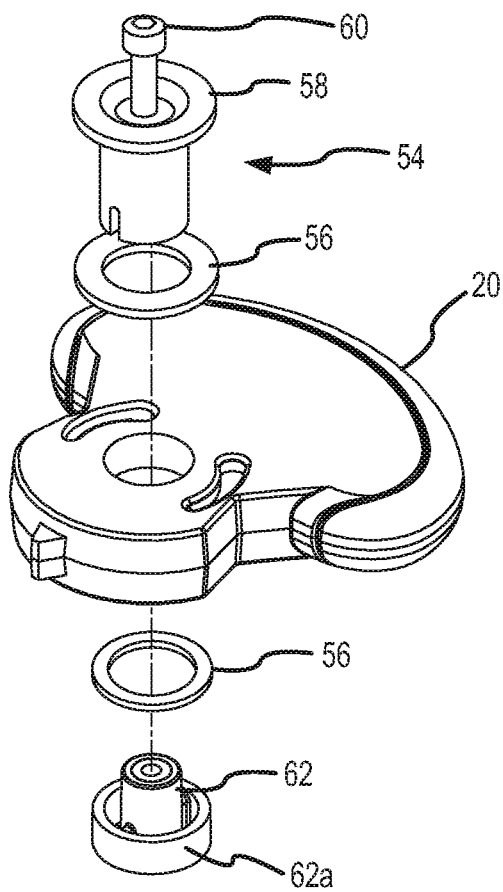
FIG. 12 is an isometric view of an auto-lock mechanism with the auto-lock mechanism exploded to better illustrate its various components.
Figure 12A:
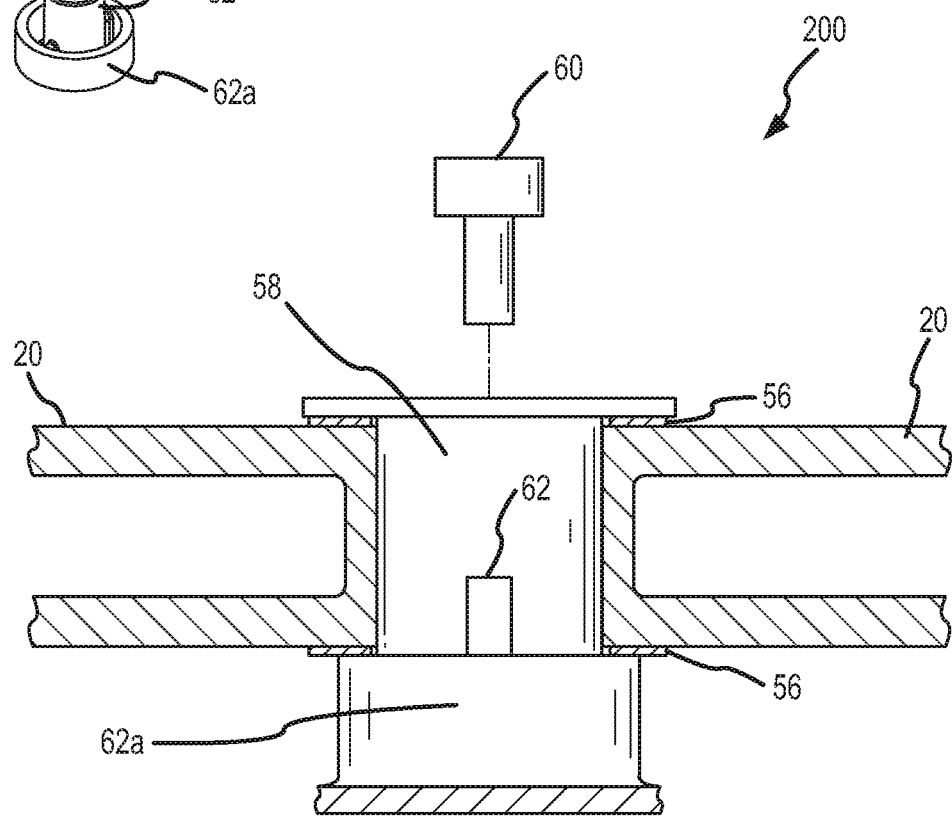
FIG. 12A is side cutout view of the auto-lock mechanism of FIG. 12.

As shown in FIGS. 2, 12 and 12A, in operation a washer 56 is optionally placed on the landing 62a. The actuator 20 is then placed over the pivot base 62 and onto the washer 56 or the landing 62a. An optional washer 56 can be placed on the actuator 20. The bushing 58 is threaded through the washers 56, actuator 20, and pivot base 62. A hex-head screw 60 is then threaded through the bushing 58, the washers 56, the actuator 20, and is tightened into the pivot base 62. It is preferable that the bushing 58 fit closely over the pivot base 62 so as to prevent excessive lateral motion between the bushing 58 and the pivot base 62 during rotational motion of the actuator 20. Likewise, it is preferable that the actuator 20 fit closely over the bushing 58 to prevent lateral motion between the bushing 58 and the actuator 20 during rotational motion of the actuator 20.

The screw 60 will be tightened during manufacturing to create a tension T. T is determined by considering several factors, and will vary from application to application, but must be a sufficient tension to counteract the distal end's bias towards its zero position. At the same time, if T is too large the operator will be forced to exert great pressure to actuate the catheter, which is undesirable. Typical commercially available catheters today require 2-10 pounds of thumb force from the operator on the actuation handle to deflect the distal end in a desired direction. For example, a catheter may require 3 pounds of thumb force. In such a case, depending on the catheter construction, the deflected distal end 18 may exert 2-3 pounds of force towards its neutral or zero position. Accordingly, the tension T is set sufficiently large to counteract that force, e.g., 3 or more pounds. The tension T can also be increased as necessary to give the catheter operation a desirable level of thumb force for the operator, as increasing the tension T will increase the thumb force required to operate the catheter. Once the screw 60 has been tightened to create the desired tension T, the screw 60 can be permanently or semi-permanently fixed in place by application of a locking fluid.

The bushing 58 can have notches 58a cut in its bottom portion that are designed to mate with slats 62b. The slats 62b are located in the space between the pivot point 62 and the landing 62a. When the notches 58a are joined to the slats 62b the bushing 58 is engaged such that the bushing 58 will have little rotation relative to the lower grip portion 24b, and as such the actuator 20 will have reduced "slack" to be taken up by the operator before the distal end will deflect in the desired direction. In a preferred embodiment, the bottom of the bushing 58 can have cross hatching or other patterns cut onto its outer surface to facilitate mating with, or bonding to the inside of the landing 62a.

Figure 12B:
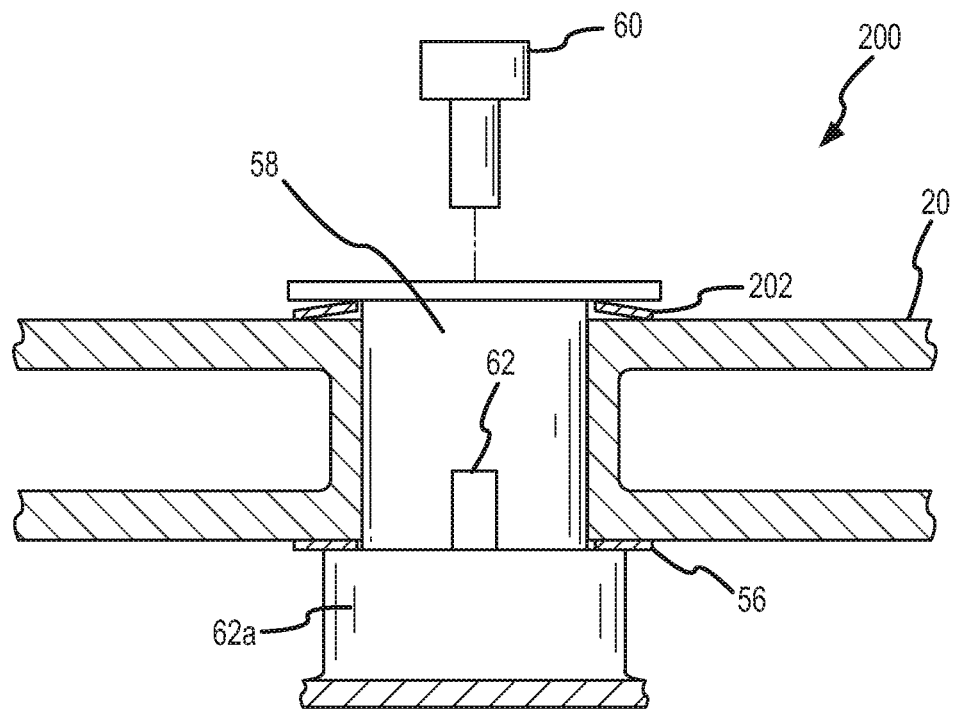
FIG. 12B is side cutout view of a modification of the auto-lock mechanism of FIG. 12.
Figure 12C:
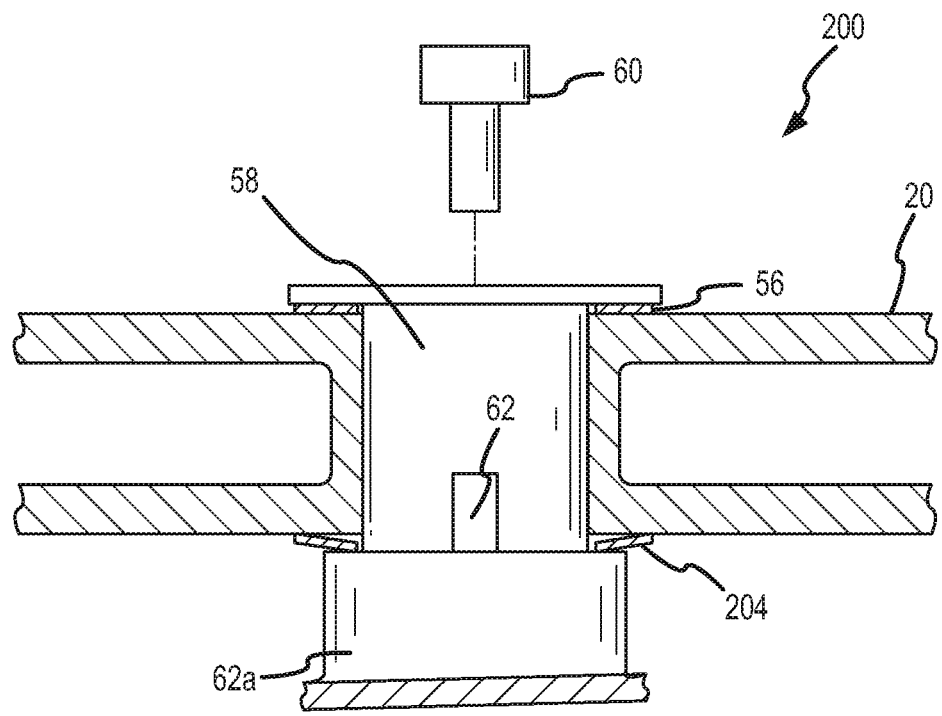
FIG. 12C is side cutout view of a modification of the auto-lock mechanism of FIG. 12.

As shown in FIGS. 12B and 12C, the auto-locking mechanism can further include a tensioning member 200. For example, as shown in FIG. 12B, a Belleville washer 202 can be placed between the bushing 58 and the actuator 20. As shown in FIG. 12C, a Belleville washer 204 can be placed between the landing 62a and the actuator 20.

In operation, the components of the auto-locking mechanism may swell or shrink due to excessive heat or cold. The tensioning member 200 will operate to either take up the slack, or to provide room for expansion, while at the same time maintaining a constant tension T. This advantageously ensures that the operator will experience the same desirable level of thumb force to operate the actuators as set during manufacturing. Such a tensioning member could be a Belleville washer as shown in FIGS. 12B, 12C, or another tensioning apparatus. In addition to the locations shown in FIGS. 12A-12C, above, the tensioning member 200 can be placed at any other point in the auto-locking mechanism 54 where it will provide for a constant tension.

Figure 13A:
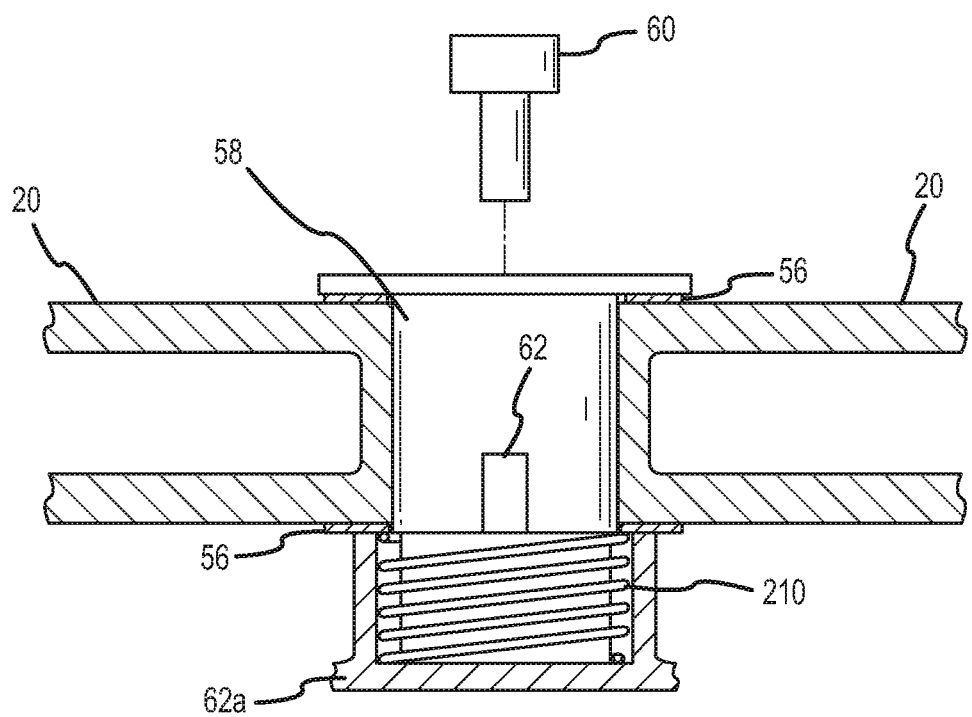
FIG. 13A is side cutout view of a modification of the auto-lock mechanism of FIG. 12.
Figure 13B:
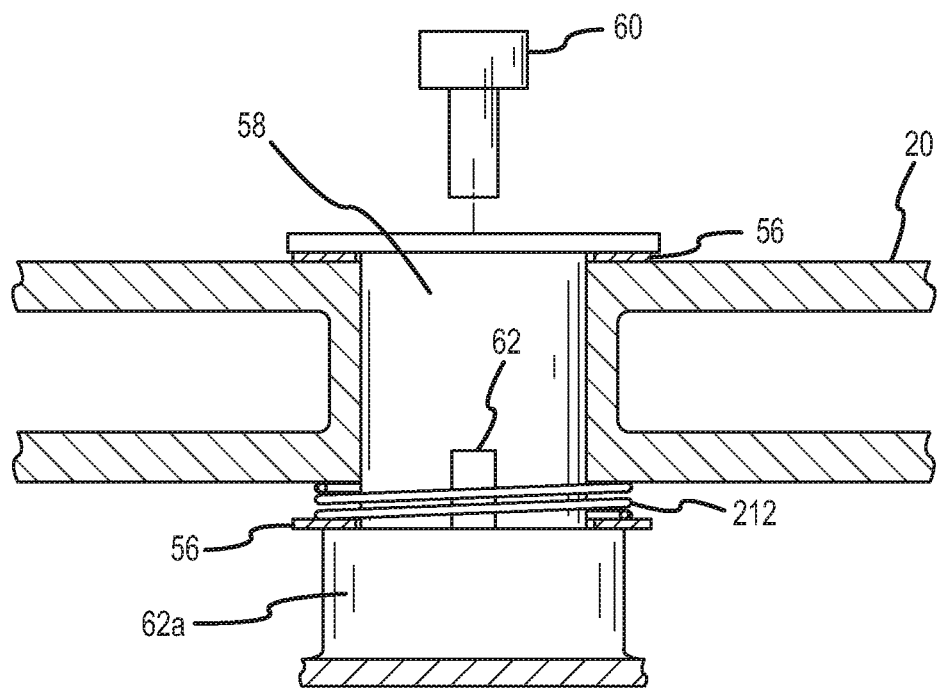
FIG. 13B is side cutout view of a modification of the auto-lock mechanism of FIG. 12.
Figure 13C:
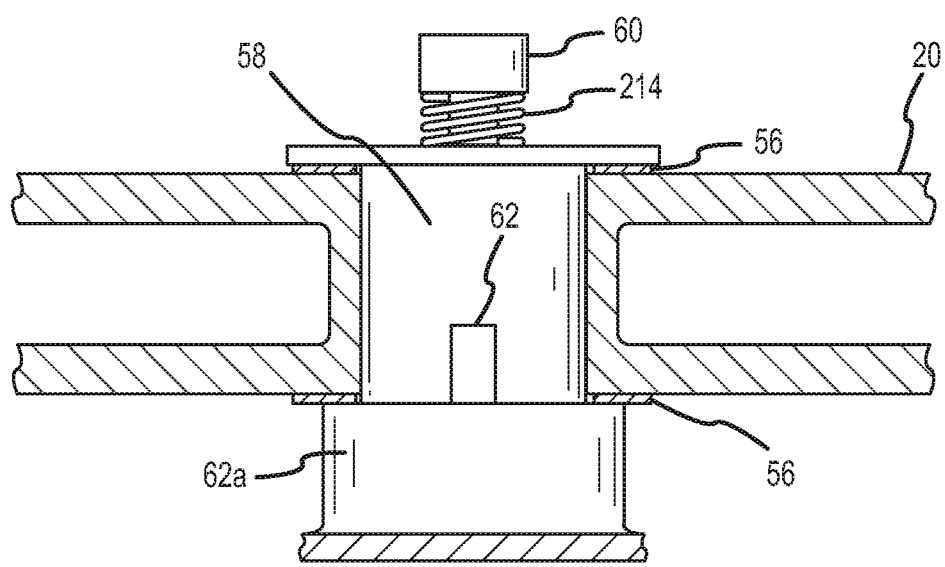
FIG. 13C is side cutout view of a modification of the auto-lock mechanism of FIG. 12.

For example, as shown in FIG. 13A, a tensioning member such as a spring 210 can be placed in a gap between landing 62a and pivot point 62. The bushing 58 can slip over the pivot point 62 and rest an optional washer 56 that rests on the spring 210. As with a Belleville washer, the spring can be located in a variety of locations, so long as it provides for a relatively constant tension T on the actuator 20 to keep a constant thumb force for moving and automatically locking the actuator 20. As shown in FIG. 13B, the spring 212 can be located between washer 56 and actuator 20, or as shown in FIG. 13C, the spring 214 can be located between the screw 60 and the bushing 58.

Figure 14:
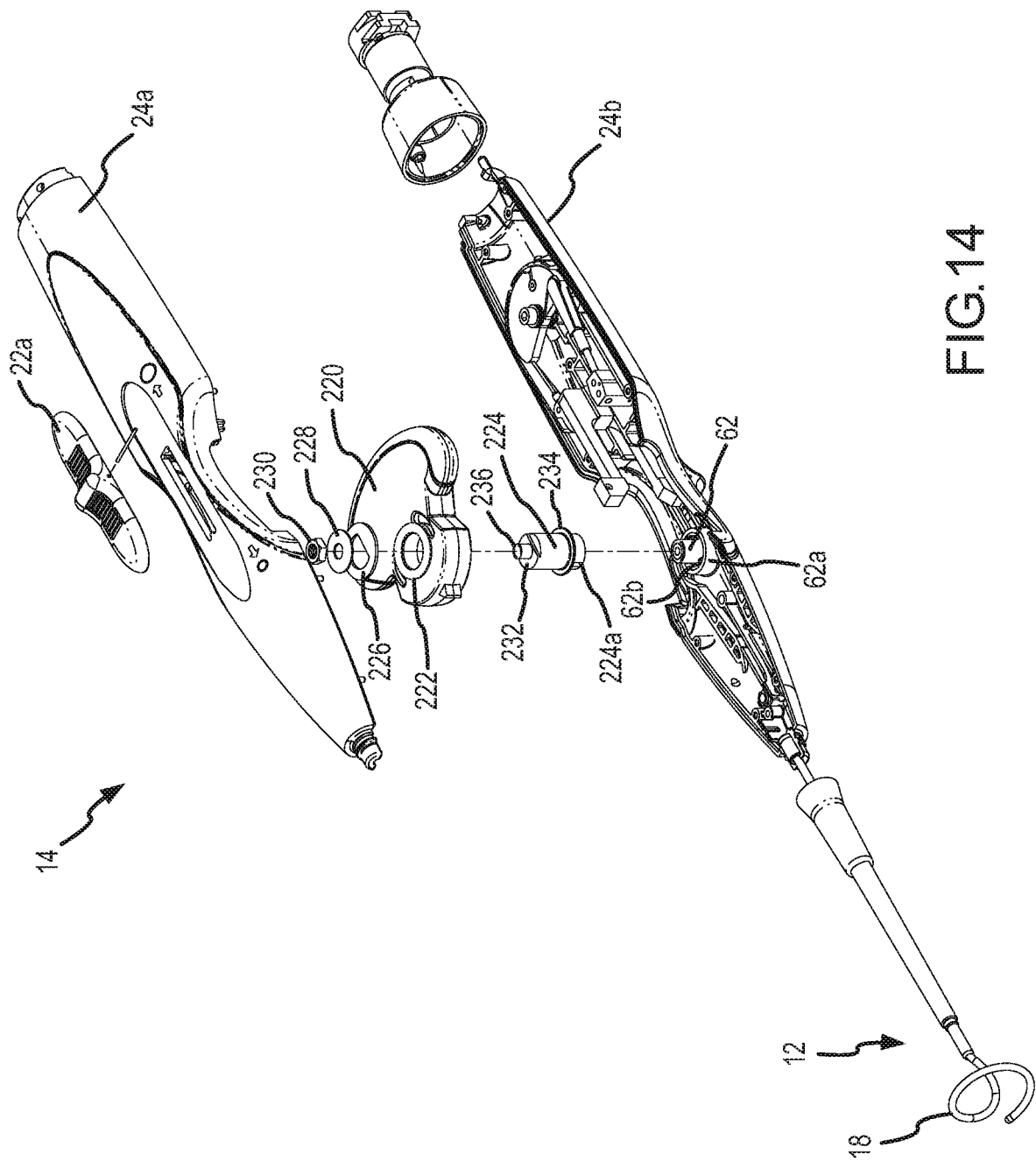
FIG. 14 is an isometric view of a second auto-lock mechanism with the auto-lock mechanism exploded to better illustrate its various components.

FIG. 14 depicts another variation of the invention, in which a bushing 224 includes notches 224a cut in its bottom portion that are designed to mate with slats 62b. The slats 62b are located in the space between the pivot point 62 and the landing 62a. When the notches 224a are joined to the slats 62b the bushing 224 is engaged such that the bushing 224 will have little rotation relative to the lower grip portion 24b, and as such the actuator 220 will have reduced "slack" to be taken up by the operator before the distal end will deflect in the desired direction. In a preferred embodiment, the bottom of the bushing 224 can have cross hatching or other patterns cut onto its outer surface to facilitate mating with, or bonding to the inside of the landing 62a. The bushing 224 can be epoxied to the pivot point 62 and/or the landing 62a.

The bushing 224 can be constructed from any material, especially a durable polymer, a stainless steel, or brass. Ideally the material selected will be sufficiently durable to endure long periods of sitting under compression tension, and also have a low frictional range allowing ready movement between the bushing 224 and the actuator components.

The bushing 224 may also have a D-shaped top surface 232. The bushing includes a bushing landing surface 234 that rests on the landing 62a. The bushing landing surface 234 and the sides of the bushing 224 may be polished, e.g., to 8 microns, to maintain cycle durability. The actuator 220 includes an integral actuation washer portion 222. The actuator 220 is slid over the bushing 224. A D-shaped washer 226 is then mated with the D-shaped top surface 232. A washer 228 rests between on the D-shaped washer 226. A nut 230 is then attached to threaded surface 236 and tightened to a tension T, e.g., 5-6 pounds of force, and a drop of thread lock is added.

In this aspect of the invention, the vertical load path advantageously runs only from bushing 224, its landing 234, through actuator 220 to D-shaped washer 226, optional washer 228, and nut 230. In particular, the load path does not include the polycarbonate upper or lower grip portions 24a, 24b, and thus does not place a long term stress on these portions.

Figure 15:
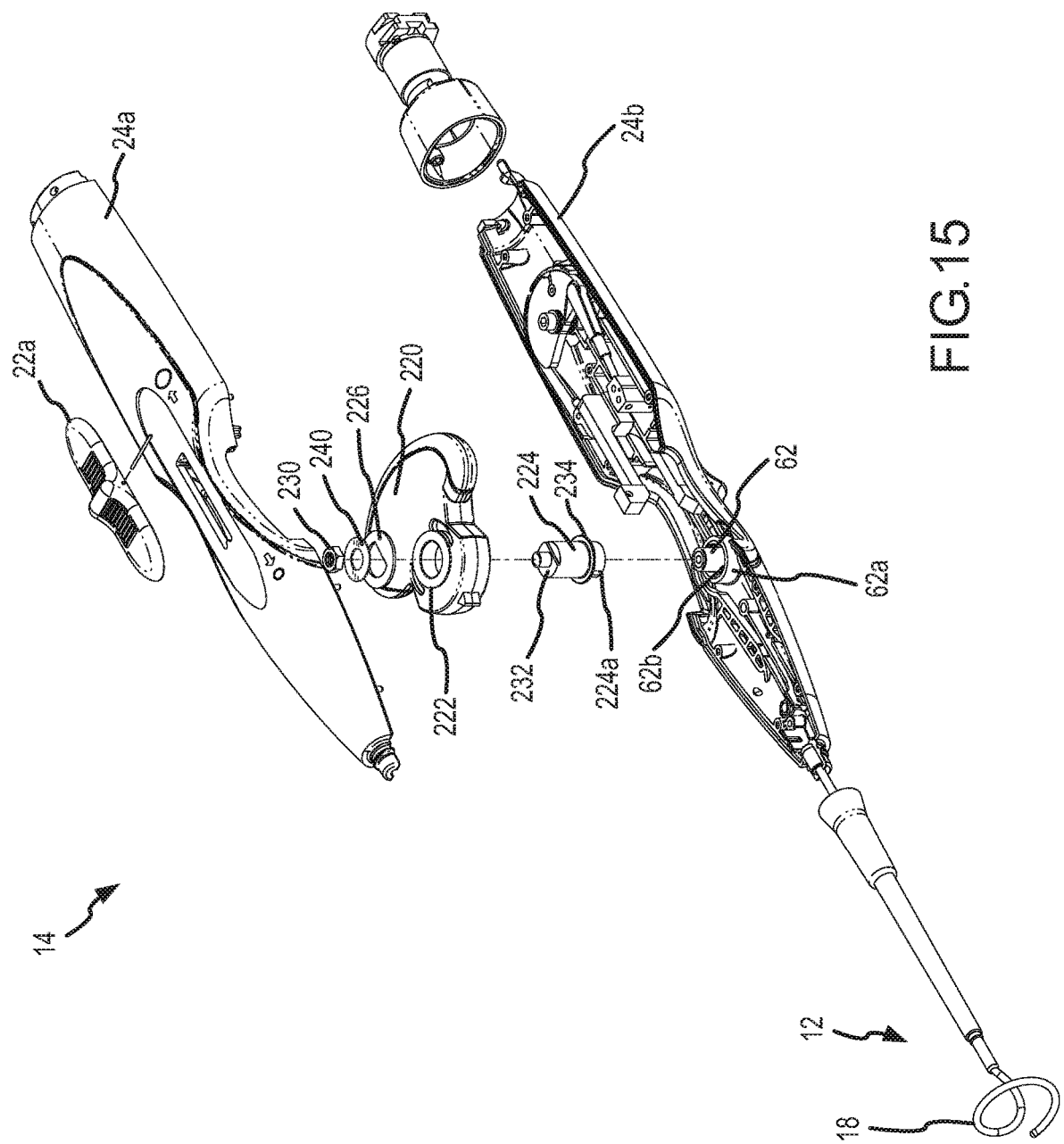
FIG. 15 is an isometric view of a variation of the second auto-lock mechanism with the auto-lock mechanism exploded to better illustrate its various components.
Figure 15A:
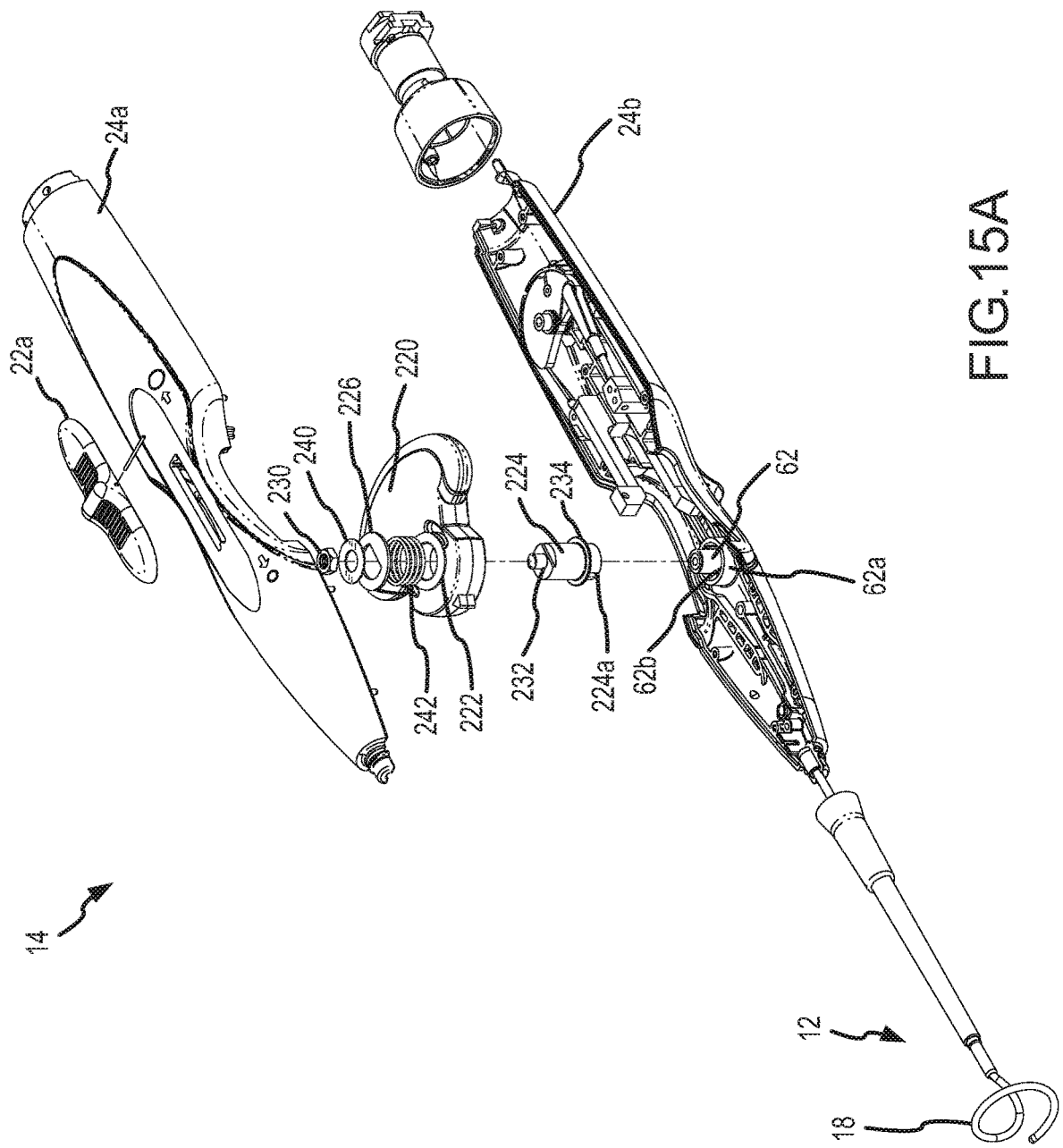
FIG. 15A is an isometric view of a variation of the second auto-lock mechanism with the auto-lock mechanism exploded to better illustrate its various components.
Figure 15B:
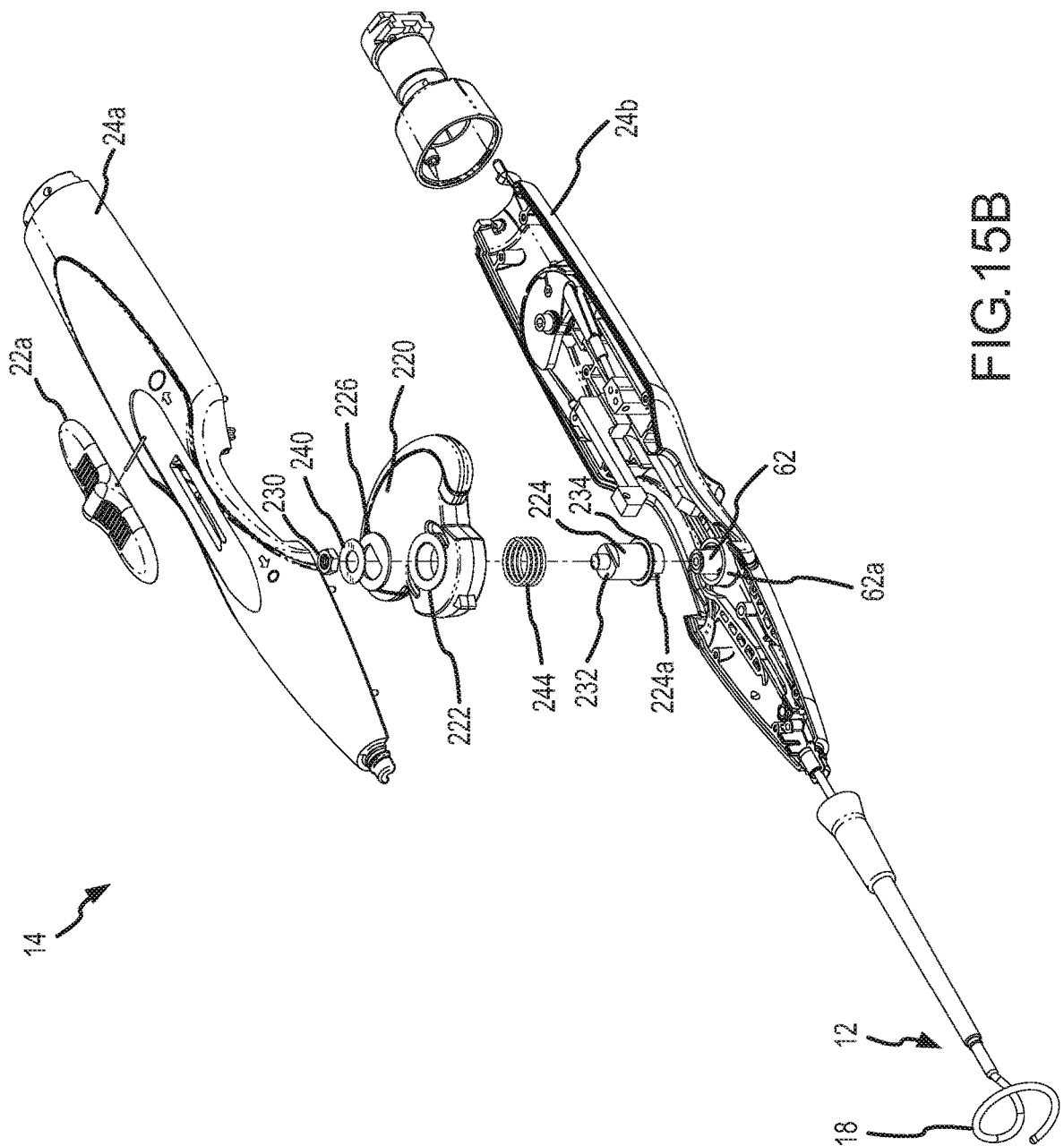
FIG. 15B is an isometric view of a variation of the second auto-lock mechanism with the auto-lock mechanism exploded to better illustrate its various components.

As shown in FIG. 15, the washer 228 may be replaced by a tensioning member such as a Belleville washer 240. Likewise, as shown in FIGS. 15A, 15B, a tensioning member such as a spring 242 or 244 may be employed. As detailed above, the tensioning member will operate to either take up the slack, or to provide room for expansion, while at the same time maintaining a constant tension T. In addition to the locations shown in FIGS. 15-15C, above, the tensioning member can be placed at any other point in the auto-locking mechanism 54 where it will provide for a constant tension.

Figure 16:
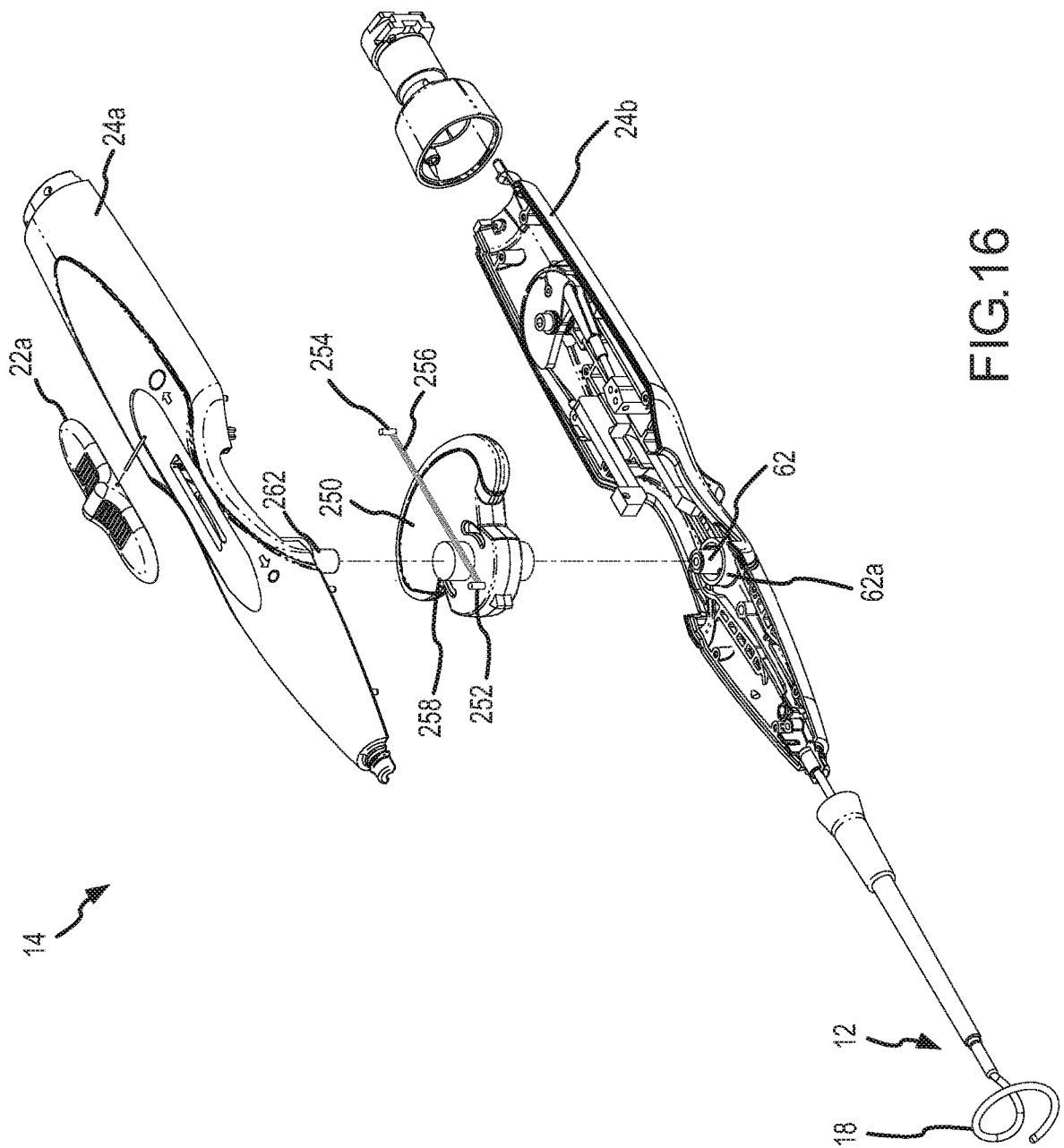
FIG. 16 is an isometric view of a third auto-lock mechanism with the auto-lock mechanism exploded to better illustrate its various components.

As shown in FIG. 16, an actuator 250 can include a post 258 designed to attach to upper and lower grip portions 24a, 24b by sliding over or otherwise attaching to pivot base 62 on lower grip portion 24b and pivot base 262 on upper grip portion 24a. Actuator 250 includes a first post 252 attached to a spring 256, e.g., a tension spring or extension spring. The spring 256 is attached to a second post 254, which is attached to lower grip portion 24b. In operation, as the actuator 250 is pivoted on post 258, the distal end 18 of the catheter is deflected, and will exert a force F toward returning to the distal end's zero point. The spring 256, actuator 250, post 252, and post 254 are placed such that the spring is at its longest when the actuator is at its middle point. When the actuator 250 is pivoted away from its middle point, the length between posts 252, 254 is shortened, thus shortening the spring 256. Thus, to return to the actuator 250's middle point, a force F1 must be exerted to lengthen the spring 256. This force F1 will oppose the force F, and preferably exceed the force F. That is, the force F generated by the distal end 18 seeks to return the distal end 18 to its zero point, and thus return the actuator 250 to its middle point. The Force F1 generated by the spring 256 seeks to move the actuator further to the left or right of its middle point, and thus move the distal end to the left or right. As a result, the spring 256 acts as a tensioning member 200 in the auto-locking mechanism. As is known to one or ordinary skill in the art, the motion of the actuator 250, spring 256, and posts 252, 254 may be aided by means of gears placed in relation to the post to lengthen or shorten the distance between the posts 252, 254 during motion of the actuator 250.

Figure 17:
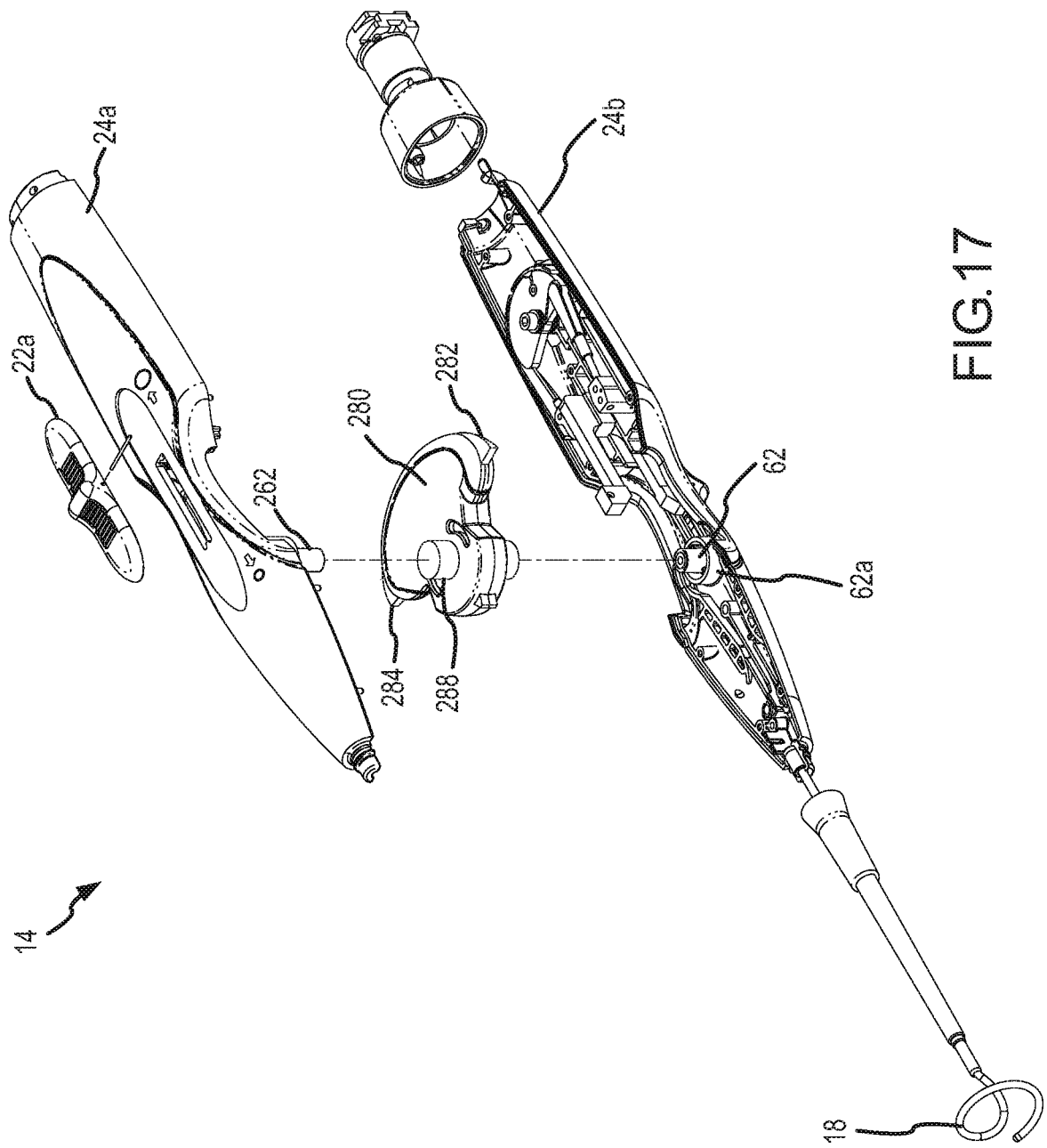
FIG. 17 is an isometric view of a fourth auto-lock mechanism with the auto-lock mechanism exploded to better illustrate its various components.

The actuator of the present invention may assume numerous physical formats, and is not limited to an actuator of the shape shown in the drawings. For example, the actuator 20 could assume a T-shape, or could be round. As shown in FIG. 17, an actuator 280 can include a post 288 designed to attach to upper and lower grip portions 24a, 24b by sliding over or otherwise attaching to pivot base 62 on lower grip portion 24b and pivot base 262 on upper grip portion 24a. The actuator 280 may have depressible levers 284, 282, which must be depressed by the operator in order for actuator 280 to pivot. The levers 284, 282 are connected to a locking mechanism inside the actuator 20 that must be released before rotational motion is possible.

Figure 18:
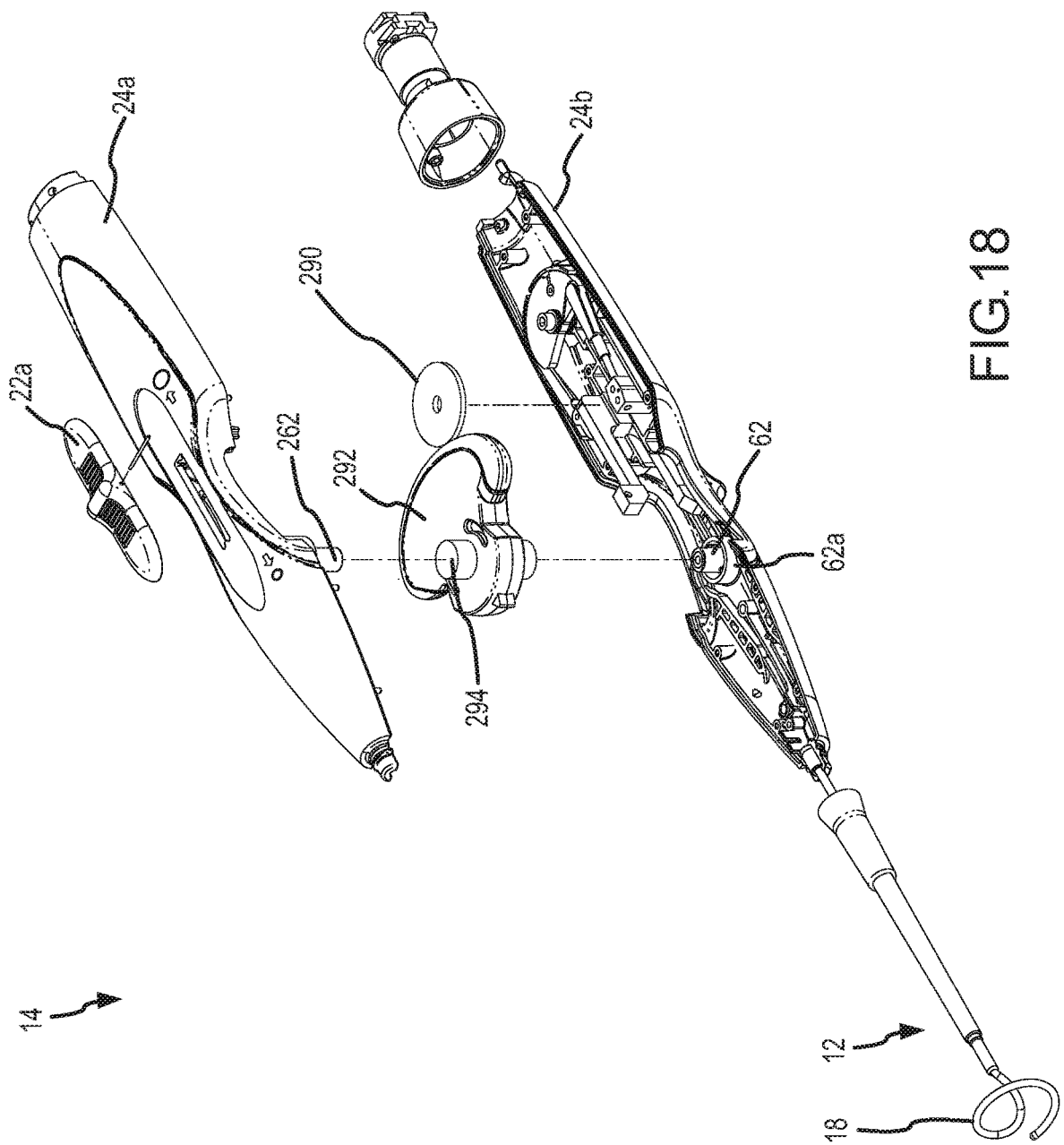
FIG. 18 is an isometric view of a fifth auto-lock mechanism with the auto-lock mechanism exploded to better illustrate its various components.

As shown in FIG. 18, a rotatable post 290 may be in frictional contact with actuator 292 on post 294. In operation, as the actuator 292 is pivoted on post 294, the distal end 18 of the catheter is deflected, and will exert a force F toward returning to the distal end's zero point. The rotatable post 290 must overcome a force F2, e.g., a frictional force, to rotate. Accordingly, the force F2 counteracts, and preferably exceeds, the force F exerted by the distal end 18. As a result, the rotatable post 290 acts as a tensioning member 200 in the auto-locking mechanism.

Although embodiments of this invention have been described above with a certain degree of particularity, those skilled in the art could make numerous alterations to the disclosed embodiments without departing from the spirit or scope of this invention. The actuator of the present invention may assume numerous physical formats, and is not limited to an actuator of the shape shown in the drawings. For example, the actuator 20 could assume a T-shape, or could be round.

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A handle for use with a catheter, the handle comprising:
 a grip portion having a longitudinally-extending centerline;
 an actuator pivotably coupled to the grip portion such that the actuator can be pivoted from a neutral position relative to the grip portion;
 a pinion gear disposed within the grip portion;
 a gear rack disposed within the grip portion, wherein the gear rack comprises:
  a first, stationary gear rack; and
  a second, movable gear rack, and
  wherein the pinion gear is positioned between and engaged with the first, stationary gear rack and the second, movable gear rack; and
 a control arm, having a proximal end and a distal end, disposed within the grip portion,
 wherein the proximal end of the control arm is mechanically engaged with the actuator and the distal end of the control arm is mechanically engaged with the pinion gear at a point laterally offset from the centerline of the grip portion such that the control arm transmits motion of the actuator to the pinion gear.

2. The handle according to claim 1, wherein the actuator further comprises a slot and the proximal end of the control arm resides in the slot.

3. The handle according to claim 2, wherein the slot is arcuate.

4. The handle according to claim 1, wherein the grip portion comprises a slot and the distal end of the control arm resides in the slot.

5. The handle according to claim 4, wherein the slot is arcuate.

6. The handle according to claim 1, wherein the pinion gear is positioned at a distal end of the gear rack when the actuator is positioned in the neutral position.

7. The handle according to claim 1, further comprising an actuation wire coupled to the gear rack such that movement of the actuator is mechanically transmitted to the actuation wire through the control arm, the pinion gear, and the gear rack.

8. A handle for use with a catheter, the handle comprising:
a grip portion having a longitudinally-extending centerline;
an actuator pivotably coupled to the grip portion such that the actuator can be pivoted from a neutral position relative to the longitudinally-extending centerline of the grip portion;
a first actuating assembly disposed within the grip portion on a first lateral side of the centerline of the grip portion, the first actuating assembly comprising:
a first pinion gear having an axial center;
a first gear rack; and
a first control arm having a proximal end and a distal end; and
a second actuating assembly disposed within the grip portion on a second lateral side of the centerline of the grip portion, the second actuating assembly comprising:
a second pinion gear having an axial center;
a second gear rack; and
a second control arm having a proximal end and a distal end,
wherein the proximal end of the first control arm is mechanically engaged with the actuator and the distal end of the first control arm is mechanically engaged with the first pinion gear at a point radially offset from the axial center of the first pinion gear such that the first control arm transmits motion of the actuator in a first direction relative to the centerline of the grip portion to the first pinion gear, and
wherein the proximal end of the second control arm is mechanically engaged with the actuator and the distal end of the second control arm is mechanically engaged with the second pinion gear at a point radially offset from the axial center of the second pinion gear such that the second control arm transmits motion of the actuator in a second direction relative to the centerline of the grip portion to the second pinion gear.

9. The handle according to claim 8, wherein the actuator comprises a first arcuate slot and a second arcuate slot opposite the first arcuate slot, and wherein the proximal end of the first control arm resides in the first arcuate slot and the proximal end of the second control arm resides in the second arcuate slot.

10. The handle according to claim 9, wherein, when the actuator is in the neutral position, the proximal end of the first control arm is positioned adjacent a distal end of the first arcuate slot and the proximal end of the second control arm is positioned adjacent a distal end of the second arcuate slot.

11. The handle according to claim 9, wherein the grip portion comprises a first arcuate slot and a second arcuate slot opposite the first arcuate slot, and wherein the distal end of the first control arm resides in the first arcuate slot and the distal end of the second control arm resides in the second arcuate slot.

12. The handle according to claim 11, wherein, when the actuator is in the neutral position, the distal end of the first control arm is positioned adjacent a distal end of the first arcuate slot and the distal end of the second control arm is positioned adjacent a distal end of the second arcuate slot.

13. The handle according to claim 8, wherein the first gear rack comprises a first stationary gear rack and a first movable gear rack and the second gear rack comprises a second stationary gear rack and a second movable gear rack.

14. The handle according to claim 13, wherein the first pinion gear is positioned between and engaged with the first stationary gear rack and the first movable gear rack and the second pinion gear is positioned between and engaged with the second stationary gear rack and the second movable gear rack.

15. The handle according to claim 8, wherein, when the actuator is in the neutral position, the first pinion gear is positioned adjacent a distal end of the first gear rack and the second pinion gear is positioned adjacent a distal end of the second gear rack.

16. The handle according to claim 8, wherein the first actuating assembly comprises a first actuation wire coupled to the first gear rack and the second actuating assembly comprises a second actuation wire coupled to the second gear rack.

* * * * *